United States Patent
El-Zahab et al.

(10) Patent No.: US 10,589,272 B2
(45) Date of Patent: Mar. 17, 2020

(54) THERMALLY-ASSISTED ACOUSTIC SEPARATION OF CELLS BASED ON THEIR STIFFNESS

(71) Applicants: Bilal El-Zahab, Miami Beach, FL (US); Ata Dolatmoradi, Miami, FL (US)

(72) Inventors: Bilal El-Zahab, Miami Beach, FL (US); Ata Dolatmoradi, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 348 days.

(21) Appl. No.: 15/463,164

(22) Filed: Mar. 20, 2017

(65) Prior Publication Data
US 2017/0266665 A1    Sep. 21, 2017

Related U.S. Application Data

(60) Provisional application No. 62/310,263, filed on Mar. 18, 2016.

(51) Int. Cl.
| | |
|---|---|
| *B01L 3/00* | (2006.01) |
| *B01D 21/28* | (2006.01) |
| *C12N 13/00* | (2006.01) |
| *C12N 1/02* | (2006.01) |

(52) U.S. Cl.
CPC ...... *B01L 3/502761* (2013.01); *B01D 21/283* (2013.01); *C12N 1/02* (2013.01); *C12N 13/00* (2013.01); *B01L 2200/0652* (2013.01); *B01L 2300/0816* (2013.01); *B01L 2300/0887* (2013.01); *B01L 2300/1822* (2013.01); *B01L 2400/0436* (2013.01); *B01L 2400/0451* (2013.01)

(58) Field of Classification Search
None
See application file for complete search history.

(56) References Cited

U.S. PATENT DOCUMENTS

| | | | |
|---|---|---|---|
| 2011/0144566 A1* | 6/2011 | Dacey, Jr. ................ | A61F 2/30 604/21 |
| 2014/0008307 A1* | 1/2014 | Guldiken .......... | B01L 3/502761 210/748.05 |
| 2015/0253226 A1* | 9/2015 | Augustsson ...... | B01L 3/502753 435/7.24 |

OTHER PUBLICATIONS

Prabhune et al., "Comparison of mechanical properties of normal and malignant thyroid cells," Micron, Mar. 27, 2012, pp. 1267-1272, vol. 43.

Xu et al., "Cell stiffness is a biomarker of the metastatic potential of ovarian cancer cells," PLOS One, Oct. 4, 2012, pp. 1-12, vol. 7, No. 10.
Li et al., "AFM indentation study of breast cancer cells," Biochemical and Biophysical Research Communications, Jul. 24, 2008, pp. 609-613, vol. 374.
Hou et al., "Deformability study of breast cancer cells using microfluidics," Biomed Microdevices, Dec. 10, 2008, pp. 557-564, vol. 11.
Swaminathan et al., "Mechanical stiffness grades metastatic potential in patient tumor cells and in cancer cell lines," Cancer Research, Aug. 1, 2011, pp. 5075-5080, vol. 71, No. 15.
Hosseini et al., "How malaria parasites reduce the deformability of infected red blood cells," Biophysical Journal, Jul. 2012, pp. 1-10, vol. 103, No. 1.
Guo et al., "Microfluidic biomechanical assay for red blood cells parasitized by plasmodium falciparum," Lab on a Chip, Dec. 19, 2011, pp. 1143-1150, vol. 12.
Aingaran et al., "Host cells deformability is linked to transmission in the human malaria parasite plasmodium falciparum," Cellular Microbiology, Apr. 12, 2012, pp. 983-993, vol. 14, No. 7.
Wandersee et al., "Dietary supplementation with docosahexanoic acid (DHA) increases red blood cell membrane flexibility in mice with sickle cell disease," Blood Cells, Molecules and Diseases, 2015, pp. 183-188, vol. 54.
Shelby et al., "A microfluidic model for single-cell capillary obstruction by plasmodium falciparum-infected arythrocytes," Proceedings of the National Academy of Sciences (PNAS), Dec. 9, 2003, pp. 14618-14622, vol. 100, No. 25.
Altschuler et al., "Cellular heterogeneity: do differences make a difference," Cell, May 14, 2010, pp. 559-563, vol. 141.
Chiou et al., "The influence of physical and physiological cues on atomic force microscopy-based cell stiffness assessment," PLOS One, Oct. 2013, pp. 1-12, vol. 8, No. 10.
Thomas et al., "Measuring the mechanical properties of living cells using atomic force microscopy," Jove: Journal of Visualized Experiments, Jun. 27, 2013, pp. 1-8, vol. 76.
Vichare et al., "Influence of cell spreading and contractility on stiffness measurements using AFM," Soft Matter, Aug. 31, 2012, pp. 10464-10471, vol. 8.
Zhou et al., "Accurate measurement of stiffness of leukemia cells and leukocytes using an optical trap by rate-jump method," RSC Advances, Jan. 2014, pp. 8453-8460, vol. 4, No. 17.
Nematbakhsh et al., "Cell biomechanics and its applications in human disease diagnosis," Acta Mechanica Sinica, 2015, pp. 268-273, vol. 31, No. 2.
Guz et al., "If cell mechanics can be described by elastic modulus: study of different models and probes used in indentation experiments," Biophysical Journal, Aug. 2014, pp. 564-575, vol. 107, No. 3.
Lekka et al., "Cancer cell recognition-mechanical phenotype," Micron, 2012, pp. 1259-1266, vol. 43.

(Continued)

*Primary Examiner* — Nghi V Nguyen
(74) *Attorney, Agent, or Firm* — Saliwanchik, Lloyd & Eisenschenk

(57) ABSTRACT

Devices, systems, and methods for separating cells or vesicles using a thermo-acoustophoretic approach are provided. A microfluidic device can be used for stiffness-based separation of cells or vesicles that otherwise have the same or approximately the same size, shape, and charge, where at least some of the membranes or vesicles have different compositions. The separation can be done by tuning the temperature of the cells or vesicles.

18 Claims, 15 Drawing Sheets

(56) References Cited

OTHER PUBLICATIONS

Lekka et al., "Cancer cell detection in tissue sections using AFM," Archives of Biochemistry and Biophysics, 2012, pp. 151-156, vol. 518.
Lee et al., "Mismatch in mechanical and adhesive properties induces pulsating cancer cell migration in epithelial monolayer," Biophysical Journal, Jun. 2012, pp. 2731-2741, vol. 102, No. 12.
Faria et al., "Measurement of elastic properties of prostate cancer cells using afm," The Analyst, Jul. 25, 2008, pp. 1498-1500, vol. 133.
Kapishnikov et al., "Continuous particle size separation and size sorting using ultrasound in a microchannel," Journal of Statistical Mechanics: Theory and Experiment, Jan. 25, 2006, pp. 1-15.
Walde et al., "Giant vesicles: preparations and applications," Chembiochem, Mar. 24, 2010, pp. 848-865, vol. 11.
Phillip et al., "The mechanobiology of aging," Annual Review of Biomedical Engineering, Author manuscript, May 31, 2016, pp. 1-34, PMC.
Lam et al., "Chemotherapy exposure increases leukemia cell stiffness," Blood, Apr. 15, 2007, pp. 3505-3508, vol. 109, No. 8.
Di Carlo, "A mechanical biomarker of cell state in medicine," Journal of Laboratory Automation, Jan. 27, 2012, pp. 32-42, vol. 17, No. 1.
Suresh, "Biomechanics and biophysics of cancer cells," Acta Materialia, 2007, pp. 3989-4014, vol. 55, Elsevier Ltd.
Suwanarusk et al., "The deformability of red blood cells parasitized by plasmodium falciparum and p. vivax," The Journal of Infectious Diseases, Jan. 15, 2004, pp. 190-194, vol. 189.
Nash et al., "Mechanical properties of oxygenated red blood cells in sickle cell (HbSS) disease," Blood, Jan. 1984, pp. 73-82, vol. 63, No. 1.
Bruus, "Acoustofluidics 7: the acoustic radiation force on small particles," Lab Chip, 2012, pp. 1014-1021, vol. 12.
Heimburg, "Mechanical aspects of membrane thermodynamics. Estimation of the mechanical properties of lipid membranes close to the chain melting transition from calorimetry," Biochimica et Biophysica Acta, Dec. 1998, pp. 147-162, vol. 1415.
Halstenberg et al., "Cholesterol-induced variations in the volume and enthalpy fluctuations of lipid bilayers," Biophysical Journal, Jul. 1998, pp. 264-271, vol. 75.
Krivanek et al., "Interaction of the antimicrobial peptide gramicidin S with dimyristoyl-phosphatidylcholine bilayer membranes: a densitometry and sound velocimetry study," Biochimica et Biophysica Acta, Feb. 2001, pp. 452-463, vol. 1510.
Laurell et al., "Chip integrated strategies for acoustic separation and manipulation of cells and particles," Chemical Society Reviews, 2007, pp. 492-506, vol. 36.
Hood et al., "Alignment of particles in microfluidic systems using standing surface acoustic waves," Applied Physics Letters, Jan. 30, 2008, pp. 044104-1-044104-3, vol. 92.
Li et al., "Acoustic separation of circulating tumor cells," Proceedings of the National Academy of Sciences of the United States of America (PNAS), Apr. 21, 2015, pp. 4970-4975, vol. 112, No. 16.
Grenvall et al., "Concurrent isolation of lymphocytes and granulocytes using prefocused free flow acoustophoresis," Author manuscript, Analytical Chemistry, Jun. 2, 2015, pp. 1-16.
Burguillos et al., "Microchannel acoustophoresis does not impact survival or function of microglia, leukocytes or tumor cells," PLOS One, May 27, 2013, pp. 1-11, vol. 8, No. 5.
Mabrey et al., "Investigation of phase transitions of lipids and lipid mixtures by high sensitivity differential scanning calorimetry," Proceedings of the National Academy of Sciences of the United States of America, Nov. 1976, pp. 3862-3866, vol. 73, No. 11.
Dimova et al., "Pretransitional effects in dimyristoylphosphatidylcholine vesicle membranes: optical dynamometry study," Biophysical Journal, Jul. 2000, pp. 340-356, vol. 79, No. 1.
Woodka et al., "Lipid bilayers and membrane dynamics: insight into thickness fluctuations," Physical Review Letters, Aug. 3, 2012, pp. 058102-1-058102-5, vol. 109, No. 5.

Schaefer et al., "Cell-stiffness-induced mechanosignaling—a key driver of leukocyte transendothelial migration," Journal of Cell Science, 2015, pp. 2221-2230, vol. 128, The Company of Biologists Ltd.
Nakazawa et al., "A role of the cancer cell membrane fluidity in the cancer metastases: an ESR study," Tohoku Journal of Experimental Medicine, 1989, pp. 193-198, vol. 157.
Fenner et al., "Macroscopic stiffness of breast tumors predicts metastasis," Scientific Reports, Jul. 1, 2014, pp. 1-8, vol. 4, No. 5512.
Tziakas et al., "Total cholesterol content of erythrocyte membranes is increased in patients with acute coronary syndrome: a new marker of clinical instability," Journal of the American College of Cardiology, May 29, 2007, pp. 2081-2089, vol. 49, No. 21.
Kojima, "Molecular aspects of the plasma membrane in tumor cells," Nagoya Journal of Medical Science, 1993, pp. 1-18, vol. 56.
Li et al., "Elevated levels of cholesterol-rich lipid rafts in cancer cells are correlated with apoptosis sensitivity induced by cholesterol-depleting agents," American Journal of Pathology, Apr. 2006, pp. 1107-1118, vol. 168, No. 4.
Hager et al., "The role of cholesterol in prostate cancer," Current Opinion in Clinical Nutrition and Metabolic Care, Aug. 2006, pp. 379-385, vol. 9.
Cortes et al., "Advances in the physiological and pathological implications of cholesterol," Biological Reviews, Feb. 2013, pp. 1-19.
Ballas et al., "Rheologic predictors of the severity of the painful sickle cell crisis," Blood, Oct. 1988, pp. 1216-1223, vol. 72, No. 4.
Schulze et al., "Stiffening of human skin fibroblasts with age," Biophysical Journal, Oct. 2010, pp. 2434-2442, vol. 99, No. 8.
Lee et al., "Biomechanics approaches to studying human diseases," Trends in Biotechnology, Mar. 2007, pp. 111-118, vol. 25, No. 3.
Needham et al., "Structure and mechanical properties of giant lipid (DMPC) vesicle bilayers from 20° C. below to 10° C. above the liquid crystal-crystalline phase transition," Biochemistry, Oct. 1988, pp. 8261-8269, vol. 27, No. 21.
Schrader et al., "Compressibility of lipid mixtures studied by calorimetry and ultrasonic velocity measurements," The Journal of Physical Chemistry B, Jun. 2002, pp. 6581-6586, vol. 106, No. 25.
Yang et al., "Acoustophoretic sorting of viable mammalian cells in a microfluidic device," Analytical Chemistry, Nov. 2012, pp. 10756-10762, vol. 84.
Thevoz et al., "Acoustophoretic synchronization of mammalian cells in microchannels," Analytical Chemistry, Apr. 2010, pp. 3094-3098, vol. 82, No. 7.
Cheng, "A theoretical description of phase diagrams for nonideal lipid mixtures," Biochimica et Biophysica Acta, Aug. 1980, pp. 358-366, vol. 600, No. 2.
Shimshick et al., "Lateral phase separation in phospholipid membranes," Biochemistry, Jun. 1973, pp. 2351-2360, vol. 12, No. 12.
Van Dijck et al., "Miscibility properties of binary phosphatidylcholine mixtures," Biochimica et Biophysica Acta, Oct. 1977, pp. 58-69, vol. 470, No. 1.
Seto et al., "Bending modulus of lipid bilayers in a liquid-crystalline phase including an anomalous swelling regime estimated by neutron spin echo experiments," The European Physical Journal E, Apr. 2008, pp. 217-223, vol. 26.
Yi et al., "Bending elasticity of saturated and monounsaturated phospholipid membranes studied by the neutron spin echo technique," Journal of Physics: Condensed Matter, Mar. 2009, pp. 1-7, vol. 21.
Wang et al., "Micromechanics of isolated sickle cell hemoglobin fibers: bending moduli and persistence lengths," Journal of Molecular Biology, Jan. 2002, pp. 601-612, vol. 315.
Shen et al., "Single cell stiffness measurement at various humidity conditions by nanomanipulation of a nano-needle," Nanotechnology, Mar. 2013, pp. 1-9, vol. 24.
Kamakura et al., "Unified description of second-order phenomena in sound waves," Electronics and Communications in Japan, Part 3, Jan. 1999, pp. 76-82, vol. 82, No. 2.
Pons et al., "Liposomes obtained by the ethanol injection method," International Journal of Pharmaceutics, Jun. 1993, pp. 51-56, vol. 95.

(56) References Cited

OTHER PUBLICATIONS

Barabino et al., "Sickle cell biomechanics," Annual Review of Biomedical Engineering, May 2010, pp. 345-367, vol. 12.

Van Blitterswijk et al., "Differences in membrane lipid composition and fluidity of transplanted GRSL lymphoma cells, depending on their site of growth in the mouse," Biochimica et Biophysica Acta, Dec. 1984, pp. 521-529, vol. 778.

Allard et al., "Red cell deformability changes in hemolytic anemias estimated by diffractometric methods (ektacytometry)," Red Cell Rheology, 1978, pp. 209-221.

Bessis et al., "Laser diffraction patterns of sickle cells in fluid shear fields," Red Cell Rheology, 1978, pp. 225-235.

Dormandy et la., "Red cell filterability after myocardial infarction," Scandinavian Journal of Clinical and Laboratory Investigation, 1981, pp. 195-198, vol. 41, Suppl. 156.

Brown et al., "Changes in blood filtrability and platelet aggregability in patients with aortic valve replacements," Clinical Hemorheology, 1989, pp. 139-147, vol. 9, No. 1.

Ekestrom et al., "Decreased red cell deformability following open-heart surgery," Scandinavian Journal of Thoracic and Cardiovascular Surgery, 1983, pp. 41-44, vol. 17.

Hirayama et al., "Evaluation of red cell damage during cardiopulmonary bypass," Scandinavian Journal of Thoracic and Cardiovascular Surgery, 1985, pp. 263-265, vol. 19.

Hirayama et al., "Changes in red cell deformability associated with anaesthesia and cardiopulmonary bypass in open-heart surgery," Scandinavian Journal of Thoracic and Cardiovascular Surgery, 1985, pp. 257-262, vol. 19.

Bareford et al., "Erythrocyte deformability in chronic renal failure," Clinical Hemorheology, 1986, pp. 501-510, vol. 6, No. 6.

Decamps et al., "Red cell filterability and chronic renal failure," Scandinavian Journal of Clinical and Laboratory Investigation, 1981, pp. 177-179, vol. 41, Suppl. 156.

Kikuchi et al., "Red blood cell deformability in renal failure," Nephron, 1982, pp. 8-14, vol. 30.

Inauen et al., "Erythrocyte deformability in dialysed and non-dialysed uraemic patients," European Journal of Clinical Investigation, Apr. 1982, pp. 173-176, vol. 12.

Cecchin et al., "Rheological abnormalities of erythrocyte deformability and increased glycosylation of hemoglobin in the nephrotic syndrome," American Journal of Nephrology, 1987, pp. 18-21, vol. 7.

McMillan et al., "Reduced erythrocyte deformability in diabetes," Diabetes, Sep. 1978, pp. 895-901, vol. 27.

Ernst et al., "Altered red and white blood cell rheology in type II diabetes," Diabetes, Dec. 1986, pp. 1412-1415, vol. 35.

Juhan et al., "Effects of insulin on erythrocyte deformability in diabetics—relationship between erythrocyte deformability and platelet aggregation," Scandinavian Journal of Clinical and Laboratory Investigation, 1981, pp. 159-164, vol. 41, Suppl. 156.

Juhan et al., "Abnormalities of erythrocyte deformability and platelet aggregation in insulin-dependent diabetics corrected by insulin in vivo and in vitro," The Lancet, Mar. 6, 1982, pp. 535-537.

Ozanne et al., "Whole blood filterability in diabetics. Influence of age, complications and duration of diabetes," Scandinavian Journal of Clinical and Laboratory Investigation, 1981, pp. 259-260, vol. 41, Suppl. 156.

Cranston et al., "Plasmodium falciparum maturation abolishes physiologic red cell deformability," Science, Jan. 1984, pp. 400-403, vol. 223.

Gor'Kov, "On the forces acting on a small particle in an acoustical field in an ideal fluid," Soviet Physics—Doklady, Mar. 1962, pp. 773-775, vol. 6, No. 9.

Dolatmoradi et al., "Thermally-assisted ultrasonic separation of giant vesicles," Lab Chip, Jul. 2016, pp. 3449-3453, vol. 16.

Ward et al., "Fundamentals of acoustic cytometry," Current Protocols in Cytometry, Jul. 2009, pp. 1-12.

Petersson et al., "Free flow acoustophoresis: microfluidic-based mode of particle and cell separation," Analytical Chemistry, Jul. 2007, pp. 5117-5123, vol. 79, No. 14.

Shields et al., "Elastomeric negative acoustic contrast particles for capture, acoustophoretic transport, and confinement of cells in microfluidic systems," Langmuir, Mar. 2014, pp. 3923-3927, vol. 30.

Pan et al., "Cholesterol perturbs lipid bilayers nonuniversally," Physical Review Letters, May 2008, pp. 1-4, vol. 100, No. 19.

Almeida et al., "Lateral diffusion in the liquid phases of dimyristoylphosphatidylcholine/cholesterol lipid bilayers: a free volume analysis," Biochemistry, Jul. 1992, pp. 6739-6747, vol. 31, No. 29.

Lande et al., "The incidence of painful crisis in homozygous sickle cell disease: correlation with red cell deformability," Blood, Dec. 1988, pp. 2056-2059, vol. 72, No. 6.

Dodds et al., "Changes in red cell deformability and other haemorheological variables after myocardial infarction," British Heart Journal, May 1980, pp. 508-511, vol. 44.

Nash et al., "Abnormalities in the mechanical properties of red blood cells caused by plasmodium falciparum," Blood, Aug. 1, 1989, pp. 855-861, vol. 74, No. 2.

Lenshof et al., "Acoustofluidics 8: applications of acoustophoresis in continuous flow microsystems," Lab Chip, Feb. 24, 2012, pp. 1210-1223, vol. 12.

Heimburg et al., "On soliton propagation in biomembranes and nerves," Proceedings of the National Academy of Sciences of the United States of America, Jul. 12, 2005, pp. 9790-9795, vol. 102, No. 28.

Tarini et al., "Ambient occlusion and edge cueing to enhance real time molecular visualization," IEEE Transactions on Visualization and Computer Graphics, Sep./Oct. 2006, pp. 1237-1244, vol. 12, No. 5.

Heller et al., "Molecular dynamics simulation of a bilayer of 200 lipids in the gel and in the liquid-crystal phases," The Journal of Physical Chemistry, Feb. 23, 1993, pp. 8343-8360, vol. 97, No. 31.

Hofsäß et al., "Molecular dynamics simulations of phospholipid bilayers with cholesterol," Biophysical Journal, Apr. 2003, pp. 2192-2206, vol. 84, No. 4.

Tierney et al., "Elasticity and phase behavior of DPPC membrane modulated by cholesterol, ergosterol, and ethanol," Biophysical Journal, Oct. 2005, pp. 2481-2493, vol. 89, No. 4.

Gracia et al., "Effect of cholesterol on the rigidity of saturated and unsaturated membranes: fluctuation and electrodeformation analysis of giant vesicles," Soft Matter, Feb. 8, 2010, pp. 1472-1482, vol. 6.

Sankaram et al., "Cholesterol-induced fluid-phase immiscibility in membranes," Proceedings of the National Academy of Sciences of the United States of America, Oct. 1991, pp. 8686-8690, vol. 88.

Mateo et al., "Liquid-crystalline phases of cholesterol/lipid bilayers as revealed by the fluorescence of trans-parinaric acid," Biophysical Journal, Mar. 1995, pp. 978-987, vol. 68.

Krivanek et al., "Effect of cholesterol and ergosterol on the compressibility and volume fluctuations of phospholipid-sterol bilayers in the critical point region: a molecular acoustic and calorimetric study," Biophysical Journal, May 2008, pp. 3538-3548, vol. 94, No. 9.

Alberts et al., "Membrane structure," Molecular Biology of the Cell, Nov. 2014, pp. 565-596, Sixth edition, Garland Science.

Heimburg, "Lipid melting," Thermal Biophysics of Membranes, Sep. 2007, pp. 75-97, First edition, Wiley-VCH.

Marsh, "Phase diagrams: binary and ternary mixtures," Handbook of Lipid Bilayers, Feb. 2013, pp. 601-765, Second edition, CRC Press.

Pabst et al., "Membrane medicine," Liposomes, Lipid Bilayers and Model Membranes from Basic Research to Application, Mar. 2014, pp. 217-245, First edition, CRC Press.

Gennis, "The structures and properties of membrane lipids," Biomembranes: Molecular Structure and Function, Dec. 1988, pp. 36-84, Springer.

Tien et al., "Fundamental aspects of biological membranes," Membrane Biophysics: As Viewed from Experimental Bilayer Lipid Membranes, Nov. 2000, pp. 23-82, First edition, Elsevier Science.

Phillips et al., "Biological membranes: life in two dimensions," Physical Biology of the Cell, Oct. 2012, pp. 427-480, Second edition, Garland Science.

(56) References Cited

OTHER PUBLICATIONS

Hata et al., "Alzheimer's disease as a membrane-associated enzymopathy of β-amyloid precursor protein (APP) secretases," Lipids and Cellular Membranes in Amyloid Diseases, May 2011, pp. 177-194, First edition, Wiley-VCH.

* cited by examiner

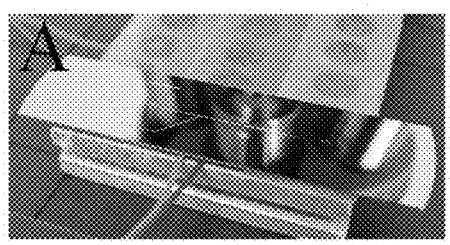
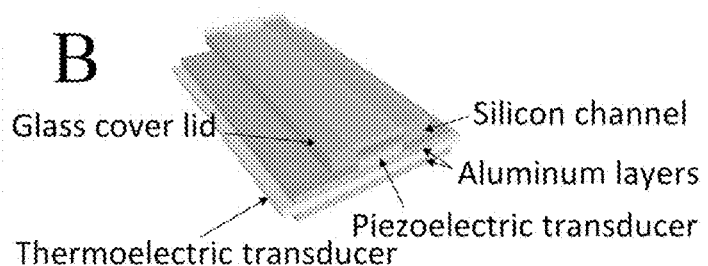
FIG. 6A          FIG. 6B
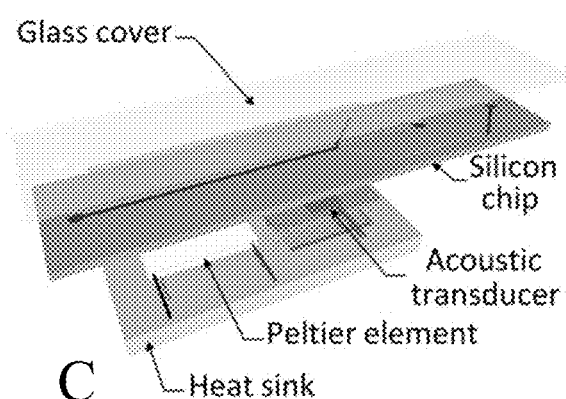
FIG. 6C

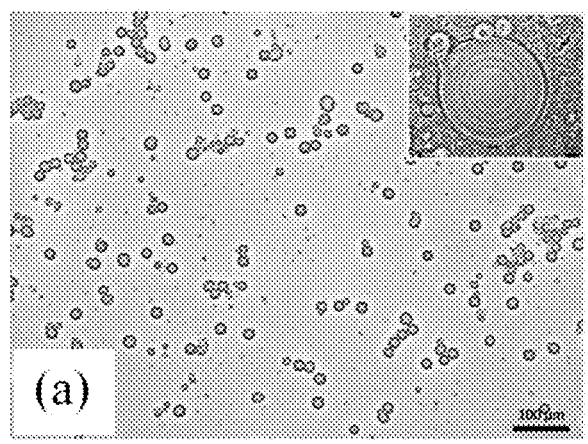
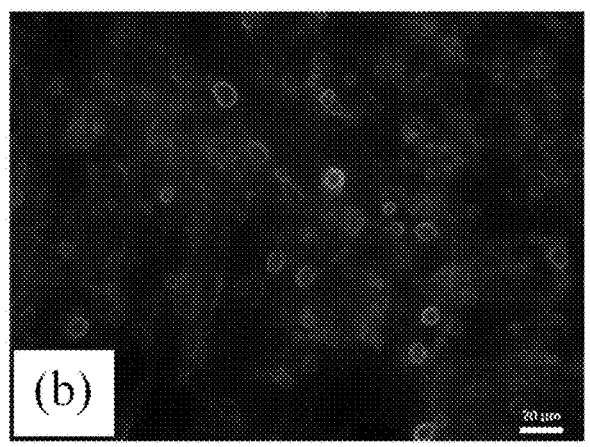
FIG.7A  FIG. 7B
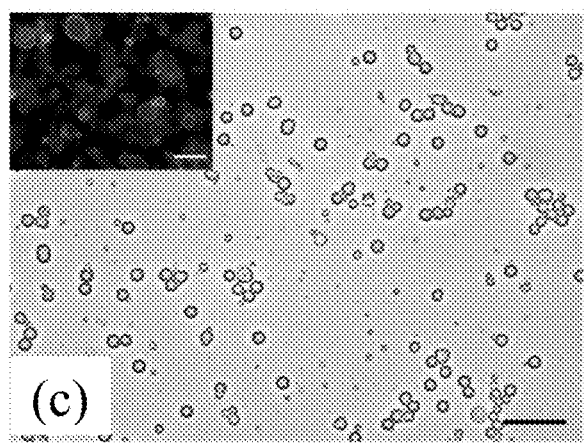
FIG. 7C

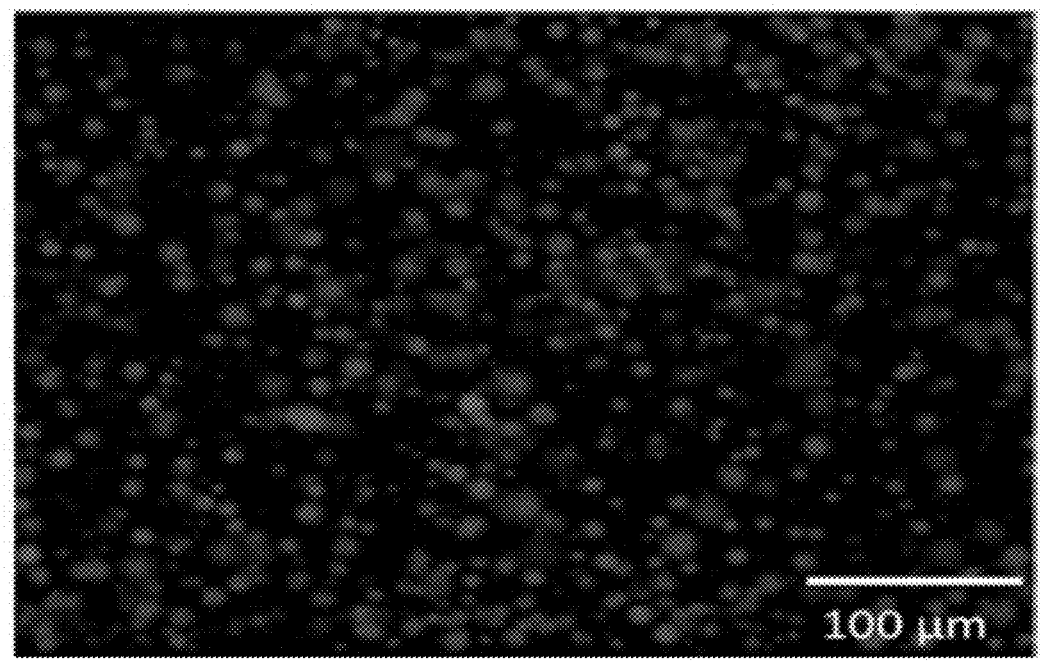
FIG. 9
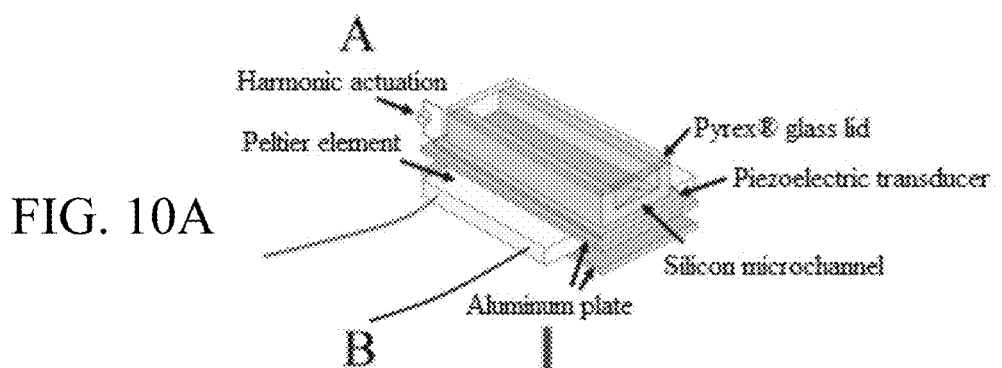
FIG. 10A
FIG. 10B
FIG. 10C

THERMALLY-ASSISTED ACOUSTIC SEPARATION OF CELLS BASED ON THEIR STIFFNESS

CROSS-REFERENCE TO RELATED APPLICATION

This application claims the benefit of U.S. Provisional Application Ser. No. 62/310,263, filed Mar. 18, 2016, which is incorporated herein by reference in its entirety, including any figures, tables, and drawings.

GOVERNMENT SUPPORT

This invention was made with government support under GM061347 awarded by the National Institutes of Health. The government has certain rights in the invention.

BACKGROUND

Biomechanical properties of cells are important markers for stages in various diseases, such as invasiveness in cancers, cellular mutations, viral infections, and red blood cell anemia. Conventional methods for separation of cells can be inefficient, have low throughput, or be overly complex.

BRIEF SUMMARY

Embodiments of the subject invention provide advantageous devices, systems, and methods for separating cells (e.g., mammalian, yeast, fungus, and bacteria cells) or vesicles (e.g., lipids, liposomes, exosomes, artificial drugs, and gene delivery vehicles) using a thermo-acoustophoretic approach. A device, such as a microfluidic device, can be used for stiffness-based separation of cells or vesicles that otherwise have the same or approximately the same size, shape, and charge, where at least some of the membranes or vesicles have different stiffness values. That is, devices, methods, and systems of embodiments of the subject invention can separate cells or vesicles that have the same (or approximately the same) shape, charge, and size but different acoustic compressibility, which is inversely proportional to the stiffness of the cell or vesicle. The separation can be done by, for example, tuning the temperature of the cells, vesicles, or system as a whole. In some embodiments of the subject invention, the terms "vesicles" and "cells" can be used interchangeably, as vesicles and cells are both, essentially, lipid bilayer membranes encapsulating aqueous cores (e.g., cytoplasm of a cell).

In an embodiment, a method of separating vesicles can include: providing a population of vesicles suspended in an aqueous medium including vesicles having the same or approximately the same size, shape, and charge but different compositions to a microfluidic device; applying standing-wave acoustic signals set to the first harmonic frequency of the suspended vesicles to the device; and tuning the temperature of the device to separate vesicles based on their directions of migration as a response to the applied acoustic signals.

In another embodiment, a microfluidic device capable of accommodating (or configured to accommodate) acoustic separation of vesicles can include: a microfluidic channel etched on a silicon wafer, wherein the channel can include one inlet and at least one outlet for fluid injection and withdrawal; an optically transparent cover slip placed atop the microfluidic channel; at least one acoustic transducer bonded to the back of the microfluidic channel and connected to an AC signal generator; at least one thermoelectric transducer (e.g., a Peltier element) positioned in thermal contact with the microfluidic channel for controlling the temperature of the channel; and an aluminum heat sink placed underneath the at least one thermoelectric transducer.

BRIEF DESCRIPTION OF THE DRAWINGS

FIG. 6A shows a close-up image of an experimental setup showing chip and electrical connections of the piezoelectric and thermoelectric transducers. FIG. 6B shows a schematic view of different parts of a thermo-acoustophoretic device according to an embodiment of the subject invention. FIG. 6C is a schematic exploded view of an embodiment of the separation device in a different view.

FIG. 7A shows a transmission-mode optical micrograph of vesicles used. FIG. 7B shows a fluorescent image of the same sample shown in FIG. 7A. FIG. 7C shows an optical micrograph of DMPC vesicles with a scale bar of 100 µm. The inset shows an image of the vesicles in a fluorescent view with a scale bar of 15 µm.

FIG. 9 shows a fluorescent image of a population of vesicles with an average diameter of approximately 8 µm. The scale bar is 100 µm.

FIG. 10A shows a schematic view of a separation device equipped with a piezoelectric transducer and a thermoelectric element (e.g., a Peltier element). FIG. 10B shows a 2.5D view of the relative fluorescence intensity of vesicles focused in the middle of a channel. FIG. 10C shows a 2.5D view of the same vesicles of FIG. 10B at a slightly higher temperature.

DETAILED DESCRIPTION

Figure 1:
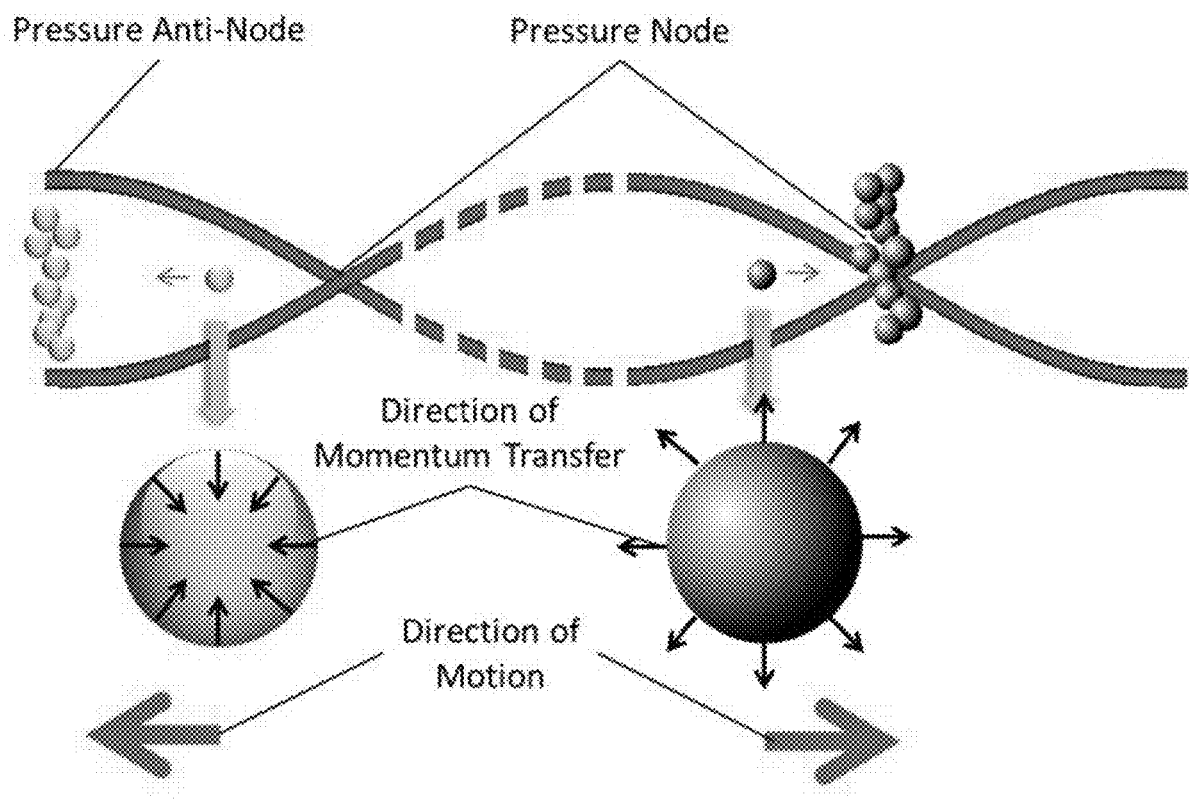
FIG. 1 is a schematic of the direction of acoustic radiation force for stiff and flexible cells in an acoustic standing-wave.

Embodiments of the subject invention provide advantageous devices, systems, and methods for separating cells (e.g., mammalian, yeast, fungus, and bacteria cells) or vesicles (e.g., lipids, liposomes, exosomes, artificial drugs, and gene delivery vehicles) using a thermo-acoustophoretic approach. A device, such as a microfluidic device, can be used for stiffness-based separation of cells or vesicles that otherwise have the same or approximately the same size, shape, and charge, where at least some of the membranes or vesicles have different stiffness values. That is, devices, methods, and systems of the subject invention can separate cells or vesicles that have the same (or approximately the same) shape, charge, and size but different acoustic compressibility, which is inversely proportional to the stiffness of the cell or vesicle. The separation can be done by, for example, tuning the temperature of the cells, vesicles, or system as a whole.

In some embodiments, methods of separating vesicles can include: providing a population of vesicles suspended in an aqueous medium including vesicles having the same or approximately the same size, shape, and charge but different compositions to a microfluidic device; applying standing-wave acoustic signals set to the first harmonic frequency of the suspended vesicles to the device; and tuning the temperature of the device to separate vesicles based on their directions of migration as a response to the applied acoustic signals.

In some embodiments of the subject invention, the terms "vesicles" and "cells" can be used interchangeably, as vesicles and cells are both lipid bilayer membranes encapsulating aqueous cores (e.g., cytoplasm of a cell).

Advantageously, methods and devices of embodiments of the subject invention can be used to separate systems comprising multiple compositions of vesicles or cells in a label-free, non-destructive manner towards applications such as, for example, the separation of cells affected by diseases that affect the cellular stiffness, such as cancers (e.g., breast cancer and prostate cancer), infections, mutations, and certain anemia of the red blood cells.

Related art acoustic separation has been in existence for a few decades without any practical applications. The main reason for this lack of application is that acoustic separation often competes with more efficient, high throughput, or otherwise simpler methods. However, related art acoustic separation methods do not take into account the fact that acoustic separation can separate based on compressibility.

As provided herein, at a specific phase transition point, the acoustic contrast factor of a homogeneous population of cells or vesicles can change signs from positive to negative, leading to an observable change in the vesicles' direction of migration. This change can be mainly due to change in the acoustic compressibility of the cell or vesicle, and the acoustic compressibility is inversely proportional to cellular stiffness. The acoustic contrast temperature, corresponding to the temperature at which the acoustic contrast factor switches signs, is unique to the composition of the cell or vesicle. This unique temperature signature allows separation of cells or vesicles with distinct membrane stiffness with a very high separation efficiency (e.g., 98.5% or greater, 99% or greater, or 99.9% or greater).

Embodiments of the subject invention can accomplish acoustic separation of vesicles by conducting a temperature sweep of the vesicles suspension. Lipids within the vesicle membrane undergo a transition shift at unique contrast temperatures, and embodiments of the subject invention can take advantage of these unique signatures to exploit these differences by operating a microfluidic device at a separation temperature between the contrast temperatures of individual vesicle types.

In cells, the lipid bilayer membrane is the common underlying structure that confines the cytoplasm and cellular organelles and gives cells their unique physical and mechanical properties, such as size, density, and stiffness. Cellular stiffness is one of the main physical changes that take place in cells during their stages of aging, death, immune-response, treatment, or transition to a diseased state. Changes in the cellular membrane stiffness have been associated with numerous cancers, viral diseases, and red blood cell disorders. In many cancer cells (e.g., breast cancer cells and prostate cancer cells), the stiffness of the cell, k (in kPa), has been shown to decrease from normal cells and benign cancer cells as it transitions to more invasive cancer types.

Table 1 summarizes reported literature data regarding changes in cell membrane stiffness that occurs as a result of cancer. For example, highly invasive breast cancer cells MDA-MB-231 had a stiffness of 0.8 kPa compared to 2.26 kPa for normal breast cells 184A1. This difference was also associated with high migratory properties and increased mobility of the invasive cells. These stiffness data were measured using an atomic force microscopy technique, which is extremely low throughput but highly accurate. Similar to breast cells, prostate cells also showed a pattern indicative of lower stiffness values for prostate cancer cells compared to the healthy ones. This trend was replicated in cervical [20], ovarian [2], and urothelial cells [21]. This indicates that a biomechanical assay can not only detect cancer cells, but also determine the degree of invasiveness of these cells based on their stiffness measurements. Related art methods of measuring stiffness do not provide both throughput and accuracy concurrently. In fact, most are only usable if a uniform population of cells is present. For example, if two or more types of cells with unique stiffness signatures are present, related art methods simply report the average value with standard deviations of increase.

Embodiments of the subject invention can separate cells that have undergone changes in stiffness from their healthy counterparts, and are thus of high diagnostic value for cancer research. This is a clear advantage since related art methods for the detection of these changes mainly rely on the deformation of cells during passage through micropores, which are designed on a case-by-case basis due to the specificity to cell size and stiffness, and are therefore limited in their applications for a wide range of cells and testing conditions.

Cholesterol plays an important role in determining the stiffness of cell membranes. Unlike other lipids that self-assemble into bilayers, cholesterol molecules form nonpolar crystals. The cholesterol content in cellular membranes, denoted as the cholesterol to phospholipid molar ratio (C/PL), varies considerably among different cell types. Changes in C/PL can be an indication of pathological disorders ranging from coronary heart disease to neurodegenerative diseases, in addition to many types of malignancies. In some embodiments, vesicles comprising a mixture of lipids and cholesterol at C/PL ratios less than 1 (e.g., 0.1, 0.2, or 0.3) can be separated effectively using the methods provided herein. In some embodiments, the membranes comprise at least one sterol selected from phytosterols (e.g., campesterol, sitosterol, and stimasterol), zoosterols (e.g., cholesterol and ergosterol), and a combination thereof.

TABLE 1

Stiffness measurements of normal/benign cells compared to cancer cells of various cell types.

| Cells | Normal/Benign/Cancer | Cell type | Invasiveness | Stiffness, k (kPa) | Ref. |
|---|---|---|---|---|---|
| Breast | Normal | 184A1 | — | 2.26 ± 0.56 | [22] |
| | Benign | MCF10A | — | 1.13 ± 0.44 | [3] |
| | Benign | MCF10A | — | 1.75 ± 0.12 | [23] |
| | Cancer | MCF7 | * | 0.63 ± 0.22 | [23] |
| | Cancer | MCF7 | * | 1.24 ± 0.46 | [22] |
| | Cancer | T47D | ** | 1.20 ± 0.28 | [22] |
| | Cancer | MDA-MB-231 | **** | 0.8 ± 0.05 | [23] |
| Prostate | Normal | PZHPV-7 | — | 3.09 ± 0.84 | [21] |
| | Benign | BPH | — | 2.80 ± 0.49 | [24] |
| | Cancer | LNCaP | * | 0.46 ± 0.17 | [21], [24] |
| | Cancer | PC-3 | **** | 1.97 + 0.41 | [24] |

— Normal or benign
* Non-invasive
** Weakly invasive
*** Invasive
**** Highly-invasive At physiological conditions, cholesterol has a rigid ring structure that generally increases membrane stiffness by altering the molecular structure of the membrane. However, cholesterol molecules can alter the stiffness of cell membrane by developing various intermolecular interactions with the phospholipid bilayers of the membrane at different temperatures. For example, at temperatures lower than the physiological temperature, cholesterol generally increases the membrane fluidity, while at higher temperatures it immobilizes the phospholipid chains within a bilayer and thus stiffens the membrane. Advantageously, these temperature-dependent properties afford the opportunities to differentiate cells of different membrane compositions.

Vesicles with variable membrane compositions can also be separated using techniques and devices of the subject invention. In particular, embodiments of the subject invention provide that vesicles and cells comprising different cholesterol to phospholipid ratios (i.e., C/PL) can be separated using thermos-acoustophoresis. Advantageously, methods provided herein can be used to separate a system comprising more than one (e.g., two, three, or four) types of vesicles and cells having distinctly different membrane compositions. These compositions can be, for example, one or more types of lipids, or a mixture of lipids and cholesterol.

In an ultrasonic standing-wave, the migration direction of a suspended particle is determined according to the acoustic radiation force, which in turn is a gradient of the acoustic potential:

$$F^{rad} = -\nabla U^{rad} \quad (1),$$

where $U^{rad}$ is the acoustic potential and the particle (e.g., a vesicle or a cell) is assumed to be spherical with a diameter much smaller than the wavelength of the standing wave. For a one-dimensional standing wave of planar type, the resulting acoustic radiation force along the direction x (the transversal direction of the channel) can be then found by differentiation:

$$F_x^{rad} = 4\pi \Phi(\rho,\beta) k_x r^3 E_{ac} \sin(2k_x x) \quad (2),$$

where $\Phi$ is the acoustic contrast factor, w is the width of a channel in which the vesicles are provided, $k_x = 2\pi/\lambda$ is the wave vector where $\lambda = 2w$, r is the particle radius, $E_{ac}$ is the acoustic energy density, and x is the distance from the wall of the channel. In standing-wave acoustophoresis, the acoustic force can be used to manipulate particles based on factors that can include the size, density, and/or compressibility of both the particles and the medium. The direction of this force follows the sign of the acoustic contrast factor, Φ, given by the equation:

$$\Phi(\rho, \beta) = \frac{1}{3}\left[\frac{5\rho_p - 2\rho_0}{2\rho_p + \rho_0} - \frac{\beta_p}{\beta_0}\right], \quad (1)$$

where $\rho_v$ and $\beta_v$ are the density and compressibility, respectively, of the particles, and $\rho_m$ and $\beta_m$ are the density and compressibility, respectively, of the medium.

Figure 8:
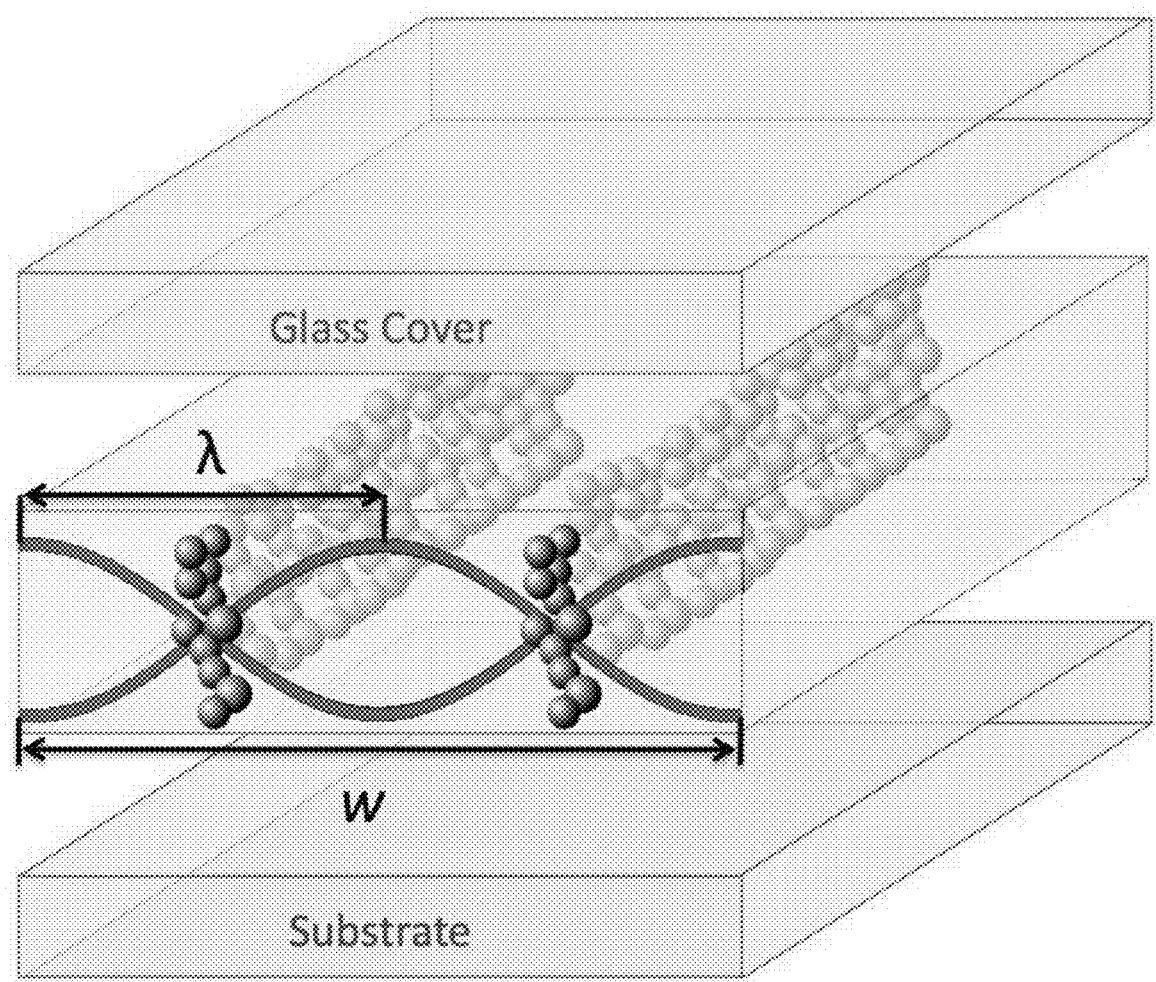
FIG. 8 shows a schematic of an acoustic patterning channel superimposed with acoustic transverse standing two-waves. The two waves inside the channel yielded two nodes and two anti-nodes. The cells were of high stiffness that focused at the pressure nodes along the length of the channel.

The acoustic contrast factor (Φ) discussed herein is proportional to the acoustic radiation force ($F^{rad}$), which consequently allows for the manipulation of particles based on the magnitude of Φ. Larger values of Φ, either positive or negative, translate to high $F^{rad}$, and as a result faster response and motion toward the energy minimum. The driving frequency f is dependent on the desired number of nodes and anti-nodes in the microlluidic channel. FIG. 8 shows a schematic of the acoustic patterning channel superimposed with the acoustic transverse standing two-waves. The two waves inside the channel yield two nodes and two anti-nodes, and in this case the cells were of higher stiffness that focused at the pressure nodes along the length of the cavity. For particles and droplets significantly smaller than the wavelength, the example shown in FIG. 8 illustrates two nodes and two anti-nodes. The driving frequency in this example is calculated depending on the width of the channel w. As shown previously that the wavelength λ of the acoustic standing wave is w/2, and subsequently, based on the speed of sound of the medium, c, the frequency is given by:

$$f = c/\lambda \quad (4).$$

The number of nodes of the standing wave inside the cavity is not limited by intrinsic attenuation, unlike a propagating sound wave. It is however, dependent on the efficiency of the reflections inside the cavity. For example, a 1 MHz sound wave inside a channel of a few millimeters to a few centimeters would experience more than 100 reflections. Important factors can include frequency, channel geometry, and the thickness and homogeneity of the adhesive layer between the transducer and the substrate. Viscosity near the solid-liquid interface is important in a flowing system in the boundary layer due to substantial velocity gradients of the fluid.

The label-free and non-destructive features afforded by standing-wave acoustophoresis provide many advantages. Related art cell separation using acoustophoresis has been restricted to separation based on size contrast instead of density or stiffness as provided by the subject invention. Related art methods conclude that cells do not vary enough in density to yield a large change in Φ to use in a separation. The subject invention, however, relies on the discovery that cellular rigidity varies drastically among cells based on their membrane composition, changing as much as 10 folds in stiffness in some instances. No related art methods or devices take advantage of this vast change for cells having the same (or approximately the same) size and shape to yield a separation in acoustophoresis.

At room temperature, cells predominantly have positive acoustic contrast factors, leading to their swift migration towards the nodal region. For that reason, the subject invention can use temperature as a new dimension in acoustophoresis to yield a change that allows opposite Φ values for different cells. This can be referred to as thermally-assisted acoustophoresis, thermo-acoustophoresis, or thermally-assisted acoustic separation of cells based on their stiffness.

No related art methods can perform cell isolation or separation on large populations of cells with the same efficiency and throughput as those provided by the subject invention, particularly not in their unaltered and viable state. Embodiments of the subject invention allow the differentiation and isolation of cells of the same or similar shape, size, charge, and density based solely on their membrane stiffness. Because each cell (or vesicle) has a unique acoustic contrast temperature (Tcp or $T_\Phi$) determined by its membrane compositions, two distinct cells (A and B, where $T_{cp,A} < T_{cp,B}$) can be separated by operating thermo-acoustophoresis at a temperature $T_{cp,A} < T_{separation} < T_{cp,B}$. Specifically, under the influence of an applied acoustic field, the A cells will migrate to the anti-nodal position (i.e., the wall of the microfluidic channel) and thus be separated from the mixture.

Advantageously, due to the label-free and non-destructive features of the separation techniques provided herein, cells can be further studied or grown post-separation. The same device can be used to perform multiple separations in series on ternary or quaternary mixtures of cells. One of the appeals of this approach is that it requires no prior knowledge of the cells.

FIG. 1 is a schematic of the direction of the acoustic radiation force for stiff (black) and flexible (blue) cells in an acoustic standing-wave. In FIG. 1, black arrows denote the direction of the momentum transfer, and the green arrows denote the direction of the net force and thus the resulting motion. Referring to FIG. 1, in a half wavelength resonator microchannel where the width of the channel w equals λ/2, where λ, is the length of the acoustic wave, the direction of the cell migration depends on the sign of Φ. Negative Φ affords anti-nodal migration, while positive Φ affords nodal migration. The main assumptions taken to derive this equation were spherical cells, smaller than the wavelength, with homogeneous physical properties.

Figure 2:
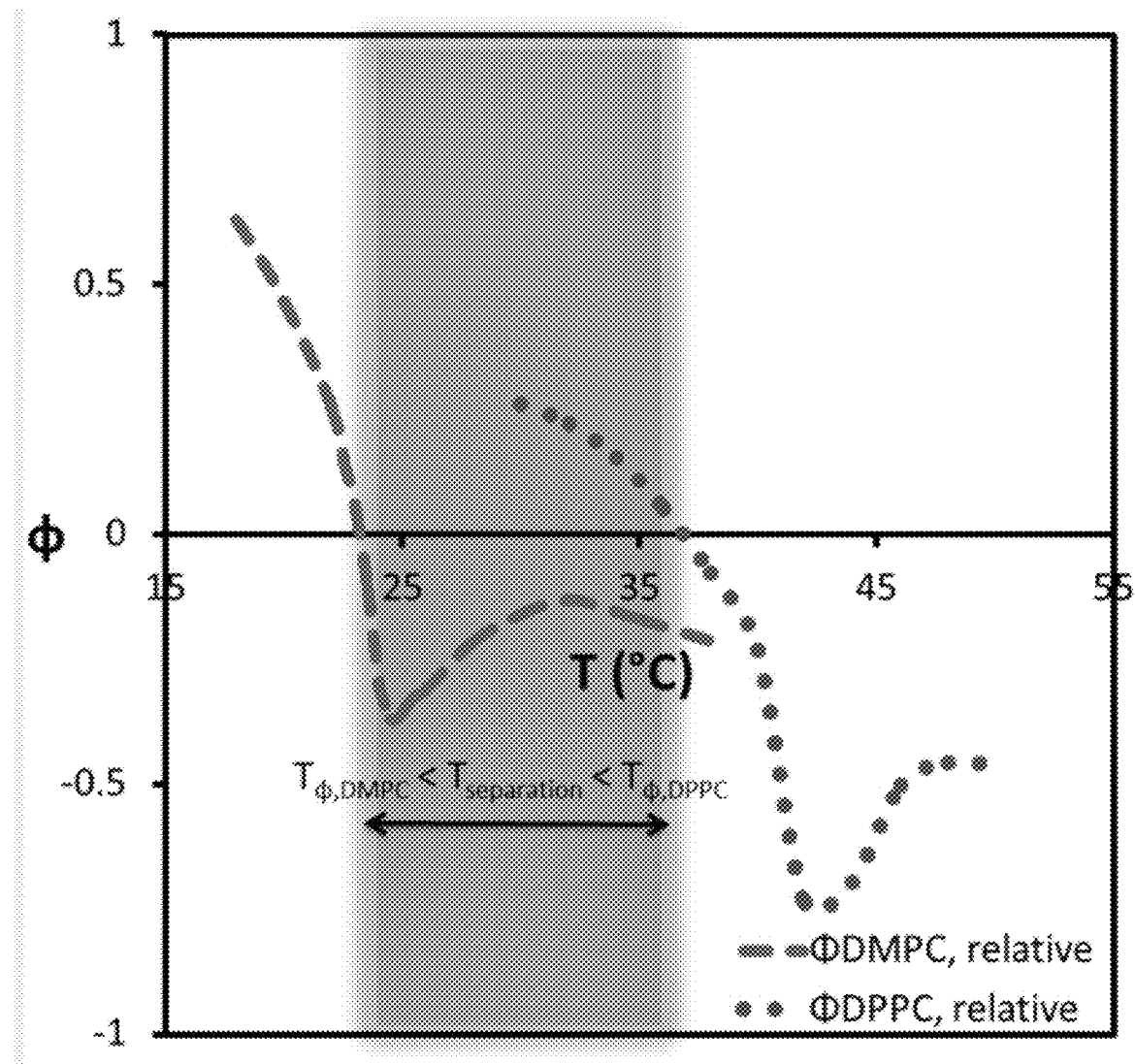
FIG. 2 shows a plot of the acoustic contrast factor ($\Phi$) versus temperature for two types of lipids, DMPC and DPPC.

FIG. 2 shows a plot of the acoustic contrast factor (Φ) versus temperature for two types of lipids, 1,2-Dimyristoyl-sn-glycero-3-phosphocholine (DMPC) and 1,2-dipalmitoyl-sn-glycero-3-phosphocholine (DPPC). Referring to FIG. 2, a value of Φ>0 indicates nodal focusing while Φ<0 indicates anti-nodal focusing. With $T_{\Phi,DMPC} < T_{separation} < T_{\Phi,DPPC}$, opposite focusing is achieved. The relative values of Φ were calculated using the data in the literature (Reference 9 in the "References" section, which is hereby incorporated by reference in its entirety).

As discussed herein, acoustophoresis is mainly sensitive to cellular density and compressibility. A change in membrane stiffness renders the cells either less or more acoustically compressible, allowing the detection of minuscule changes in real time. In embodiments of the subject invention, a temperature sweep can be used to offer a new dimension for acoustophoresis, which has not been contemplated in any related art method or device. By scanning temperature over a determined range, cells that were once considered inseparable become separable. In addition, the acoustic contrast temperature, $T_\Phi$, which is the temperature at which acoustic focusing of a given cell switches from nodal to anti-nodal, reveals valuable information about changes in cellular membrane stiffness. It is important to note that $T_\Phi$ does not correspond to a distinct phase transition; rather, it is a specific temperature at which the compressibility of the vesicles reaches a value that causes Φ to switch from positive to negative.

In some embodiments, a microfluidic device capable of accommodating (or configured to accommodate) acoustic separation of vesicles can include: a microfluidic channel etched on a silicon wafer, wherein the channel can include one inlet and at least one outlet for fluid injection and withdrawal; an optically transparent cover slip, preferably a glass cover slip, placed atop the microfluidic channel; at least one acoustic transducer bonded to the back of the microfluidic channel and connected to an AC signal generator; at least one thermoelectric transducer (e.g., a Peltier element) positioned in thermal contact with the microfluidic channel for controlling the temperature of the channel; and an aluminum heat sink placed underneath the at least one thermoelectric transducer.

Figure 11:
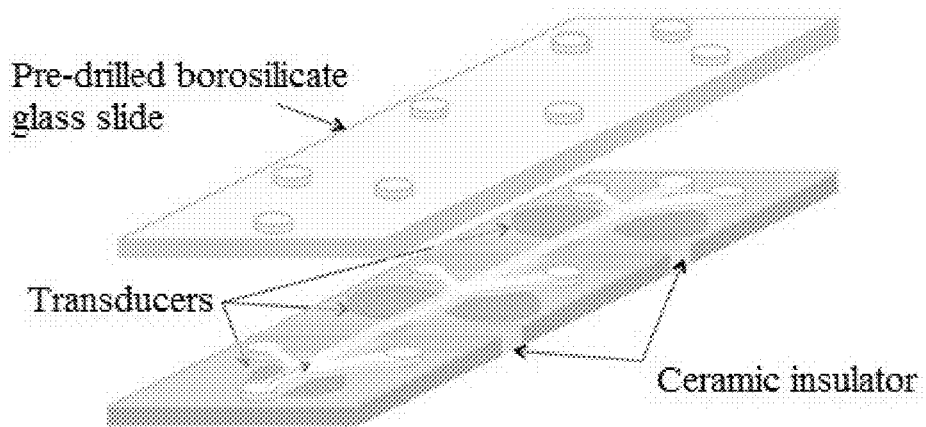
FIG. 11 shows a schematic view of a multi-stage microfluidic device according to an embodiment of the subject invention, which can perform separation of a mixture of four different types of cells or vesicles with various stiffness values.

In certain embodiments, a microfluidic device can be capable of separating (or configured to separate) cells or vesicles having more than two distinctly different compositions (e.g., tertiary, quaternary, etc. mixture). FIG. 11 shows a schematic view of such a device in which three microfluidic outlets are in sequence and separated by a thermally insulating material to allow sudden temperature changes between segments of the microfluidic device. Similarly, the device can be actuated by three separate actuators operating at three different frequencies. This design can be extended to four channels or more. Table 2 below shows a list of lipids and their corresponding melting temperatures ($T_m$). These lipids can be used as components for lipid bilayer membranes in vesicles and cells that can be separated according to embodiments of the subject invention.

Embodiments of the subject invention can, among many other advantages, help fill the knowledge gap in the relationship between the change of cellular stiffness of cancer cells and their transformation to invasive cancer cells through the use of simple, accurate, and high throughput techniques. A fundamental understanding of this phenomenon may allow the development of the right intervention to inhibit this transformation. Techniques of the subject invention can additionally allow the direct observation of the effectiveness of any such attempted intervention. In addition, the development of an isolation technique will allow cancer researchers to investigate the pathophysiology of diseased cells quickly and more reliably.

TABLE 2

List of lipids and their $T_m$ (from Avanti Polar Lipids, Inc.)

| Lipid | Family | $T_m$ (° C.) |
|---|---|---|
| 18:1t9 PC | Phosphatidylcholine | 12 |
| 22:1c13 PC | Phosphatidylcholine | 13 |
| 13:0 PC | Phosphatidylcholine | 14 |
| 16:0-18:1 PS (POPS) | Phosphatidylserine | 14 |
| 14:0 PG (DMPG) | Phosphatidylglycerol | 23 |
| 14:0 PC (DMPC) | Phosphatidylcholine | 24 |
| 16:0-18:1 PE (POPE) | Phosphatidylethanolamine | 25 |
| 16:0-14:0 PC | Phosphatidylcholine | 27 |
| 16:0-18:1 PA (POPA) | Phosphatidic Acid | 28 |
| 12:0 PE (DLPE) | Phosphatidylethanolamine | 29 |
| 18:0-14:0 PC | Phosphatidylcholine | 30 |
| 12:0 PA (DLPA) | Phosphatidic Acid | 31 |
| 15:0 PC | Phosphatidylcholine | 35 |
| 14:0-16:0 PC | Phosphatidylcholine | 35 |
| 14:0 PS (DMPS) | Phosphatidylserine | 35 |

TABLE 2-continued

List of lipids and their $T_m$ (from Avanti Polar Lipids, Inc.)

| Lipid | Family | $T_m$ (° C.) |
|---|---|---|
| 18:1t9 PE | Phosphatidylethanolamine | 38 |
| 14:0-18:0 PC | Phosphatidylcholine | 40 |

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

EXAMPLE 1

Preparation of Vesicles

In order to perform a systematic approached experiment with no interference from other properties, giant vesicles, with an average diameter of 10 μm, were prepared from various phospholipids to produce vesicles of variable membrane compositions. It is noted that vesicles are essentially lipid bilayer membranes encapsulating aqueous cores.

Using phospholipid binary mixtures with well-known thermotropic transition behavior, acoustic contrast transition due to heating or cooling of vesicle suspensions was demonstrated. Due to thermotropic phase transitions, the vesicles had an effect on their mechanical properties, especially compressibility. This effect provided tenability of the acoustic contrast factor (Φ) depending on temperature, thus enabling the existence of a temperature range in which opposite Φ signs existed. Within this temperature "window" the vesicles become mechanically distinct and thus differentiable in the acoustic radiation field, yielding separation (see also FIG. 1).

For the preparation of vesicles, three phosphatidylcholines containing linear saturated fatty acyl chains— 1,2-dimyristoyl-sn-glycero-3-phosphocholine (DMPC), 1,2-dipalmitoyl-sn-glycero-3-phosphocholine (DPPC), and 1-palmitoyl-2-oleoyl-sn-glycero-3-phosphocholine (POPC)—were obtained (Avanti Polar Lipids (Alabaster, Ala.)). All the phospholipids were used without further purification. Cholesterol was used as a stiffening agent and was purchased from Sigma-Aldrich. A 1-3 wt % solution of each lipid in the form of a lyophilized powder was first prepared in the water-miscible solvent tetrahydrofuran (≥99.9%, inhibitor-free) (Sigma-Aldrich, St. Louis, Mo.).

A fluorescent dye was introduced to the solution to label the lipid membrane of the vesicles. Dyes used in this study were Laurdan (6-dodecanoyl-2-dimethylaminonaphthalene) (AnaSpec, Inc., Fremont, Calif.), Nile red (9-diethylamino-5-benzo[α]phenoxazinone) (Acros Organics, Geel, Belgium), and CiOC6(3) iodide [3,3-dihexyloxacarbocyanine iodide] (AnaSpec, Inc). After adding the dye, distilled water was added dropwise at a rate of 10 milliliters/hour (ml/h) to the solution while the mixture was being magnetically stirred at room temperature. A syringe pump (New Era Pump Systems, Inc., Farmingdale, N.Y.) was used for the water dripping. To allow the solvent to evaporate, the sample was left open to sit in the ambient atmosphere for 24 hours. The prepared vesicles were visualized using an optical microscope (AxioCam ICc 1, Carl Zeiss Microscopy GmbH, Oberkochen, Germany) operating in transmission and reflected modes.

FIG. 7A shows a transmission-mode optical micrograph of DMPC vesicles used, displaying a uniform population of vesicles; the scale bar in FIG. 7A is 100 µm. The inset in FIG. 7A shows a giant multilamellar vesicle in higher magnification. FIG. 7B shows a fluorescent image of the same sample shown in FIG. 7A; the scale bar in FIG. 7B is 20 µM.

EXAMPLE 2

Fabrication of Microfluidic Device

The microfluidic device used as the separation device was fabricated using standard photolithography and anisotropic wet etching. The front side of a 4-inch <100> silicon wafer (WRS Materials, San Jose, Calif.) pre-coated with a, 1-µm, low-stress silicon nitride layer was first spin coated by photoresist AZ® 4620 (MicroChemicals GmbH, Ulm, Germany), followed by a soft-bake at 110° C. for 2 minutes (min). The photoresist was subsequently exposed using a contact-mode mask aligner (Model 800 MBA, OAI, San Jose, Calif.) with an exposure energy of 400 mJ/cm$^2$ and then developed using developer AZ® 400K (AZ Electronic Materials, NJ) diluted by deionized (DI) water at a volume ratio of 1:3. Upon approving the feature quality by optical microscopy (Unitron Versamet Optical Microscope, Commack, N.Y.), the residual resist inside the channel was removed by an oxygen plasma treatment (CS-1701, MARCH, Concord, Calif.). The descum procedure was performed using 100 mTorr pressure of $O_2$ and 400 Watts of power with 60 standard cubic centimeters per minute (sccm) flow rate for 45 seconds (s). The developed pattern was then etched with $CF_4$ plasma to remove the nitride layer. After doing so, the remaining photoresist was removed using a Remover PG solution (MicroChem, Newton, Mass.) kept at 65° C. for 30 min. The treatment was followed by rinsing in isopropyl alcohol and water. The underlying silicon material was then removed via wet-etch processing. A preferential silicon etchant (PSE-200) (Transene Company, Inc., Danvers, Mass.) was utilized to carry out the Si etching. In order to remove the remaining nitride layer, the wafer was washed with an aluminum etchant (Transene Company, Inc., Danvers, Mass.) for 240 min at 180° C. The wet etching was monitored and stopped when silicon was etched to the desired depth, measured using an optical profilometer (Nanovea, Irvine, Calif.). Next, the wafer was cleaned using a piranha solution, ethanol and DI water to remove any debris left from the prior processing. After rinsing and drying, the wafer was again examined using the optical microscope. Then, a 4-inch Pyrex® wafer (Praezisions Glas & Optik GmbH, Iserlohn, Germany) containing holes created manually by an ordinary drill (220-01 WorkStation™, Dremel, Racine, Wis.) was anodically bonded to the substrate via heating up the wafer at 500° C. for 15 min with 500 V of potential difference provided by a high-voltage power supply (Model 247, Keithley Instruments Inc., Cleveland, Ohio).

Figure 3A:
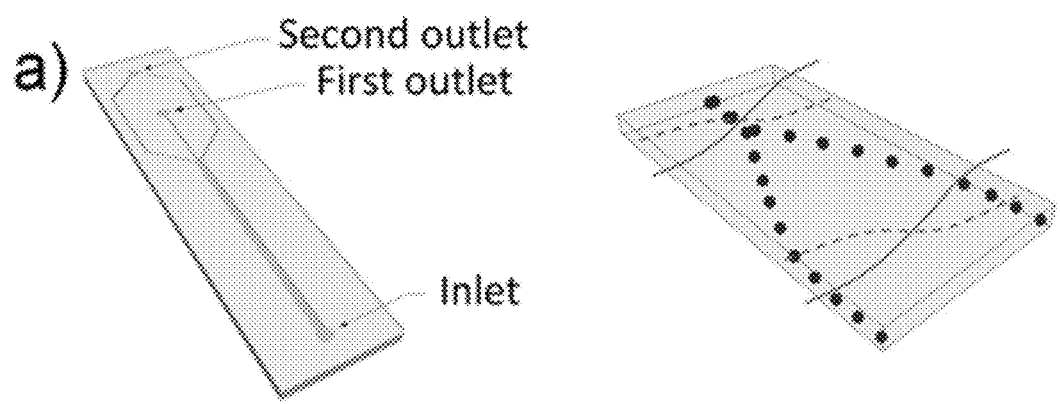
FIG. 3A shows a schematic view of a separation device according to an embodiment of the subject invention showing an overlaid acoustic half-wave.

FIG. 3A shows a schematic view of the separation device showing an overlaid acoustic half-wave.

EXAMPLE 3

Application of Microfluidic Device for Separation Experiments

For the experimental setup, the width and depth of the main channel of the device were 500 µm and 90 µm, respectively. The length of the main channel was 20 mm. A disk-shaped piezoelectric transducer (12.75 mm in diameter) with wrap-around electrode pattern (APC International, Ltd, Mackeyville, Pa.) was bonded to the back of the chip underneath the main separation channel. An AC signal of sinusoidal form was generated by a function generator (DG4062, RIGOL Technologies Inc, Beaverton, Oreg.) and then amplified by a power amplifier (Model 2348, TEGAM Inc., Geneva, Ohio). The applied voltage amplitudes were monitored using an oscilloscope (TDS 2014B, Tektronix Inc., Beaverton, Oreg.). Chip temperature was controlled throughout all experiments using a Peltier element (Farnell, London, UK), which was placed underneath the chip and connected to a DC power supply (Model 72-2010, TENMA, Washington, Ohio). An aluminum plate was used as a heat sink underneath the Peltier element.

For separation experiments, the inlet and outlet flows were controlled by syringes (BD Luer-Lok™, Franklin Lakes, N.J.) connected to two syringe pumps (New Era Pump Systems Inc., Farmingdale, N.Y.). One pump was connected to the chip inlet, infusing the vesicle specimen from a 3 mL syringe. The other pump was set in withdrawal mode and connected to two plastic syringes to control the flow in the separation chip. Both pumps were connected via PVC tubing with luer ends (TUBING LUER M-F 24", Cole-Parmer, Vernon Hills, Ill.) to the chip outlets. The average flow rate used in the separation experiments was about 5 µL/min. To conduct the separation experiments, the device was loaded onto the stage of a fluorescence microscope (Axio Scope.A1, Carl Zeiss Microscopy GmbH, Oberkochen, Germany). The concentration of the vesicle samples collected from the outlets was measured by a pre-calibrated fluorescent intensity quantification method.

FIG. 6A a close-up image of the experimental setup showing the chip and electrical connections of the piezoelectric and thermoelectric transducers. FIGS. 6B and 6C show an embodiment of the thermo-acoustophoretic device from two different views, indicating each component of the device.

Figure 3B:
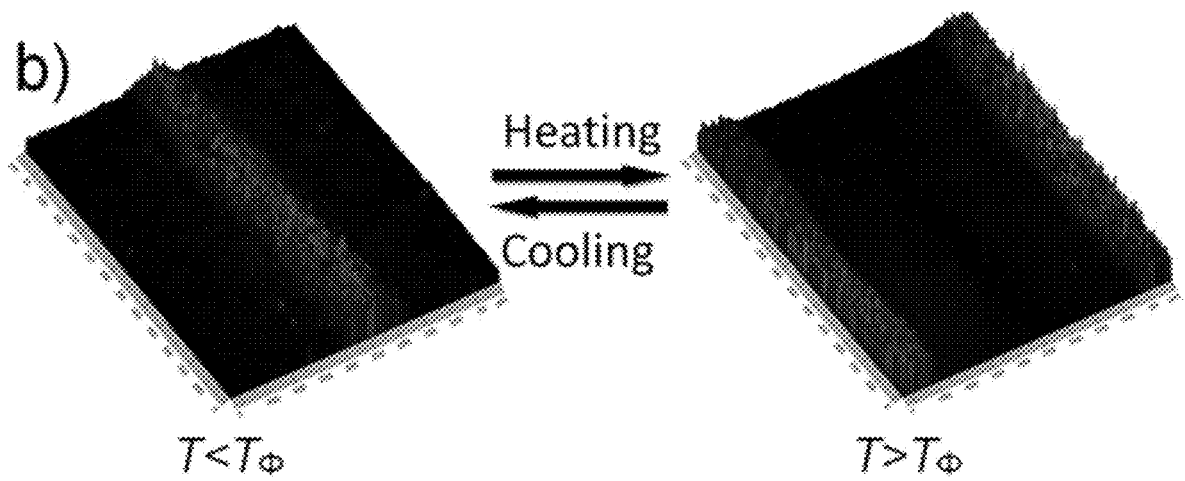
FIG. 3B shows a 2.5D view of the relative fluorescence intensity of DMPC vesicles focused in a nodal region.

In the experiments, an aqueous suspension of vesicles was continuously injected into a rectangular microfluidic channel (500 µm wide and 90 µm deep), etched in a silicon wafer as described above. The microfluidic device was fitted with a piezoelectric transducer connected to a frequency generator with adjustable sinusoidal frequency range. FIG. 3B shows a 2.5D view of the relative fluorescence intensity of the DMPC vesicles focused in nodal region at $T<T_\Phi$ and its transition to the anti-nodal region at temperature $T>T_\Phi$; $T_\Phi$ of DMPC was 23.2° C.

The chip was initially kept at a temperature as low as 1° C. in some runs with the signal generator set to the first harmonic frequency. Referring to FIG. 3B, at that frequency and temperature, the vesicles promptly focused at the nodal region located at the center of the channel. A slow sweep of temperature (1-5° C./min) was then initiated while the vesicles were visually monitored under a fluorescent microscope, as discussed above. Once the channel temperature reached or exceeded the acoustic contrast temperature, $T_\Phi$, the vesicles collectively migrated towards the anti-nodal regions, i.e. the walls in a first harmonic channel (see FIG. 3B).

EXAMPLE 4

Study of Thermo-Acoustofluidic Separation of Vesicles

Figure 4:
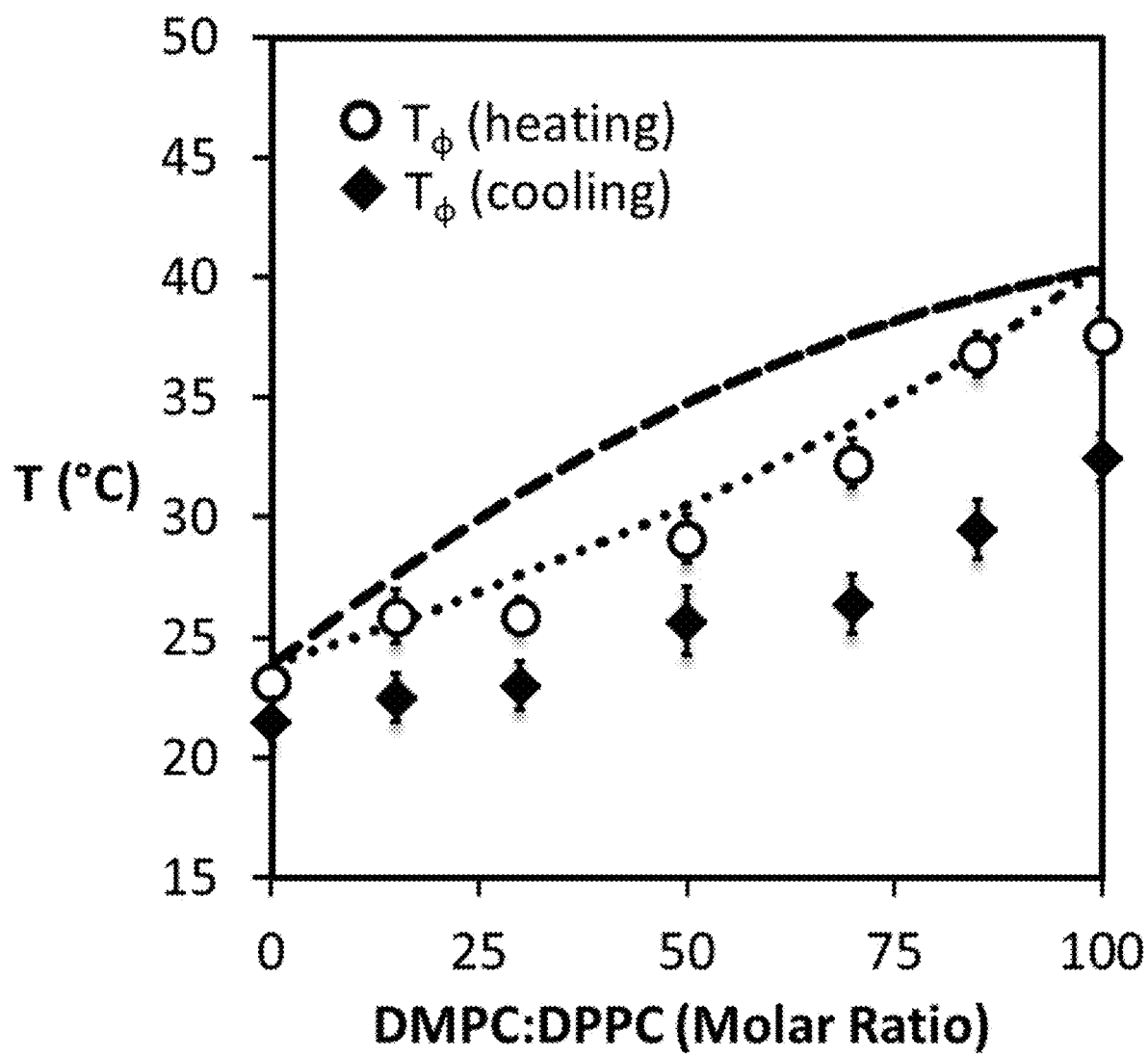
FIG. 4 shows a thermotropic isomorphous phase diagram of a lipid mixture.

FIG. 4 shows a thermotropic isomorphous phase diagram of the DMPC:DPPC lipid binary mixture. Data were obtained from the mean value of the theoretical data and the experimental data obtained by electron spin resonance (ESR) and differential scanning calorimetry (DSC) studies (solidus (dotted) and liquidus (dashed) curves). The circle markers denote the measured $T_\Phi$ during the heating experiment while diamond markers denote the measured $T_\Phi$ during the cooling curve. The heating $T_\Phi$ nearly overlapped with the solidus line over the molar ratio range.

To demonstrate the capability of thermo-acoustofluidics in the separation of vesicles, vesicles with distinct membrane compositions were prepared (DMPC, DPPC, and POPC, as discussed above). Using a modified solvent-injection method, vesicles were prepared using various molar ratios of the phospholipids DMPC ($T_m$=23.9° C.) and DPPC ($T_m$=41.4° C.). These phospholipids were shown to display discernible differences in mechanical properties before and after the main thermotropic phase transition.

Hydrated phosphatidylcholines of medium-chain size, such as DMPC and DPPC, experience a series of thermotropic transitions between different lamellar phases. At a lipid-specific temperature called the pre-transition temperature ($T_p$), the metastable or stable gel phase ($L_{\beta'}$) undergoes a transition to another gel phase known as the rippled phase ($P_{\beta'}$). On further increasing the temperature to a point known as the main transition temperature ($T_m$), the $P_{\beta'}$ gel phase converts to a fluid (or liquid-disordered) phase ($L_\alpha$). The transition temperature of interest, $T_\phi$, occurred at a temperature $T_p < T_\phi < T_m$ indicative of a mechanical transition in the membrane property rather than a distinct phase transition, namely, membrane compressibility.

Figure 12:
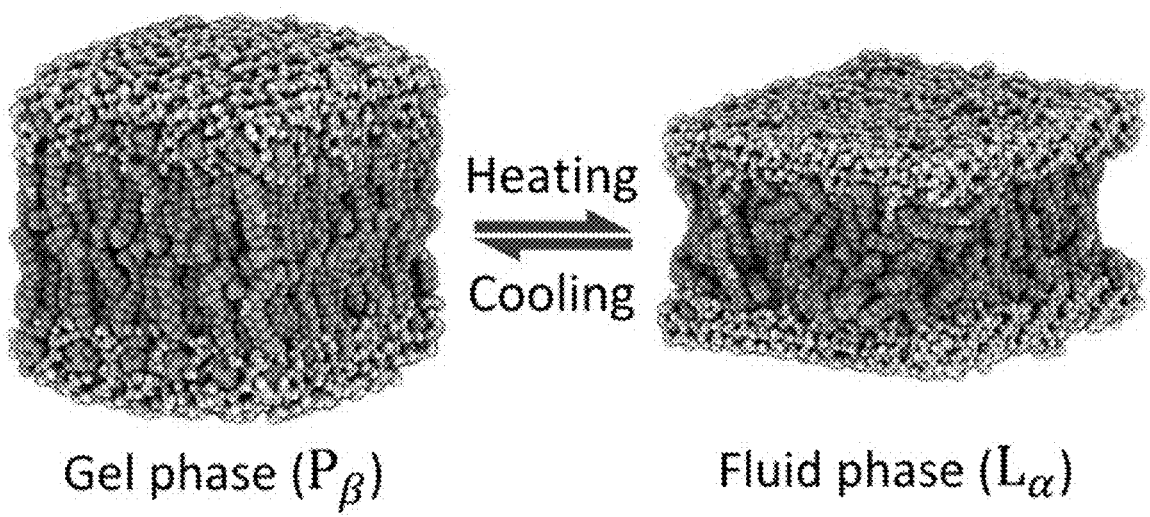
FIG. 12 is a schematic illustration of a POPC bilayer membrane in gel (ordered) and fluid (disordered) states. The bilayer is surrounded on both sides by water molecules shown in pink and white. The gray atoms on the lipid chains are the hydrogen atoms explicitly shown on the acyl chains.

For vesicles comprising POPC, however, the solid phase directly converts to the fluid phase upon heating in excess water conditions ($L_\beta \rightarrow L_\alpha$). FIG. 12 illustrates a POPC bilayer membrane in gel and fluid states constructed using QuteMol software and the coordinates data from molecular dynamic simulations provided by Heller (see references 114 and 115 in the References list herein, both of which are incorporated by reference herein in their entireties). It is expected that at the main transition from the ordered state to the disordered state the lateral crystalline arrangement and chain order of the lipid molecules are lost, resulting in expansion in volume and area as well as changes in membrane curvature. This in turn leads to considerable changes in thermoelastic properties of the membrane such as bending rigidity and compressibility.

The $T_\phi$ for various molar ratios of DMPC:DPPC vesicles were investigated for both heating and cooling transitions, both at a temperature change rate of 1° C./min. The results are shown in FIG. 4. The heating experiment showed that the transition occurred at approximately the solidus line, right before the transition from ripple to liquid phase occurred. The cooling $T_\phi$ was found to be lower, presumably due to the heat capacity in the vesicles. This temperature gap between the transitions was minimized by slowing down the temperature sweep. This transition temperature was consistent with a sudden drop of bending rigidity.

Figure 5A:
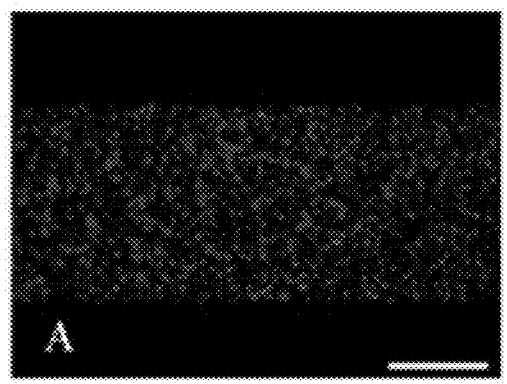
FIG. 5A shows an optical fluorescence micrograph of 100:0 DMPC:DPPC (red) and 70:30 (blue) DMPC:DPPC vesicles dispersed in an exemplary microfluidic channel at 24.5° C. with the acoustic transducer switched off.
Figure 5B:
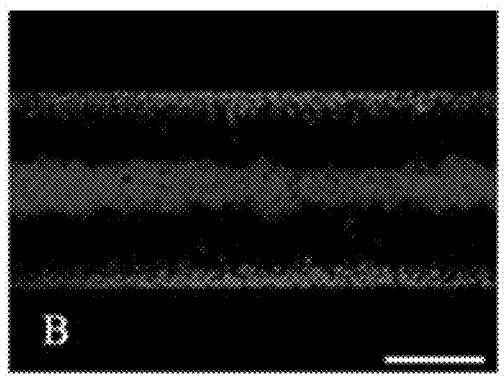
FIG. 5B show an optical fluorescence micrograph of the same vesicles in FIG. 5A after 3 seconds of the transducer switched on showing 100:0 DMPC:DPPC vesicles (red) completed migration towards the pressure anti-nodes and 70:30 DMPC:DPPC vesicles (blue) completed migration towards the pressure node. The scale bar of both micrographs is 150 µm.
Figure 5C:
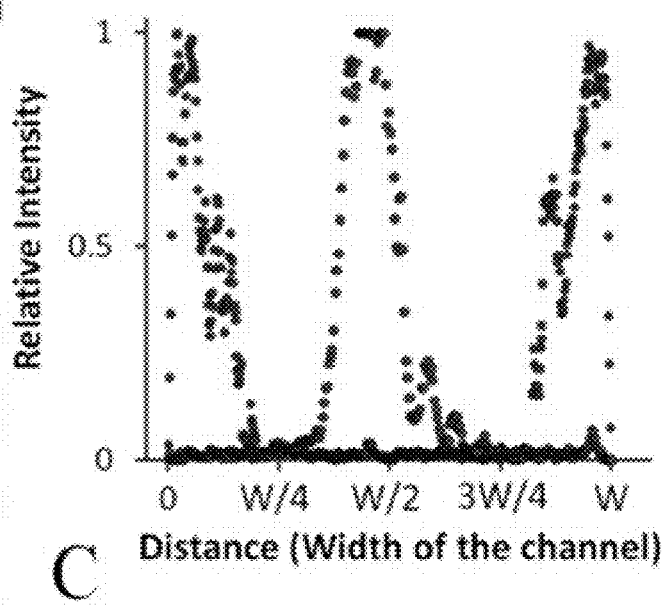
FIG. 5C shows relative fluorescence intensity scanned in the direction normal to the flow for both red and blue emissions.

FIG. 5A shows an optical fluorescence micrograph of 100:0 (red) and 70:30 (blue) DMPC:DPPC vesicles dispersed in the microchannel at 24.5° C. with the acoustic transducer switched off. FIG. 5B show an optical fluorescence micrograph of the same vesicles shown in FIG. 5A after 3 seconds of the transducer switched on showing 100:0 DMPC:DPPC completed migration towards the pressure antinodes (red; top and bottom as depicted in FIG. 5B) and 70:30 DMPC:DPPC completed migration towards the pressure node (blue; vertical center as depicted in FIG. 5B). The scale bars in both FIG. 5A and FIG. 5B are 150 μm. FIG. 5C shows a plot of relative fluorescence intensity, scanned in the direction normal to the flow, versus distance measured relative to the width of the channel (i.e., W/4 is ¼ of the width of the channel) for both red and blue emissions.

The existence of a membrane-specific temperature below which vesicles exhibit a positive $\Phi$, and above which they exhibit a negative $\Phi$ offers the possibility of separating these vesicles (see also FIG. 1). Two vesicles samples, 100:0 DMPC:DPPC and 70:30 DMPC:DPPC, were selected to demonstrate the separation. The $\Delta T_\Phi$ for these two vesicles was 2.7° C. (pure DMPC with $T_\Phi$=23.2° C. and 70:30 DMPC:DPPC ° C.). The separation temperature was selected as the approximate mid-point of 24.5° C. Referring to FIG. 5A, at this separation temperature, the mixture of vesicles was shown to be randomly dispersed in a channel that was not acoustically excited. However, referring to FIG. 5B, once the transducer was switched on (f=1.30 MHz and 50 Vpp), the separation of vesicles promptly started and completed in less 10 seconds. The distribution of vesicles can be seen in FIG. 5B with red-stained 100:0 DMPC:DPPC at the walls and the blue-stained 70:30 DMPC:DPPC at the center of the channel. Referring to FIG. 5C, this distribution was quantified using averaged fluorescent intensity in the direction normal to the flow. Using the relative intensities shown in FIG. 5C, the distribution of either type of vesicle was obtained. The 100:0 DMPC:DPPC vesicles were found to be 96.8% at the wall (within W/4 from either wall, where W is the width of the channel) and 3.2% in the central region of the channel (between W/4 and 3 W/4). Similarly, the 70:30 DMPC:DPPC vesicles were found to be 95.4% at the central region and 4.6% at the walls. With the aforementioned values, the separation factor of the two vesicle mixture was calculated as 98.5%. This separation figure of merit can be further increased by reducing the concentration of vesicles, reducing the volumetric flow rate, and/or increasing the amplitude of the acoustic radiation.

EXAMPLE 5

Additional Study of Thermo-Acoustofluidic Separation of Vesicles

An experiment similar to Example 4 was performed, and all preparation not discussed here were done as described in Example 4. FIG. 9 shows a fluorescent image of a population of DMPC vesicles used, having an average diameter of about 8 μm. FIG. 10A shows a schematic view of the separation device used, equipped with a piezoelectric transducer and a thermoelectric element. FIG. 10B shows a 2.5D view of the relative fluorescence intensity of the DMPC vesicles focused in the middle of a channel at 22.9° C. FIG. 10C shows a 2.5D view of the same vesicles of FIG. 10B at a slightly higher temperature 23.2° C., behaving differently by migrating toward the pressure antinodes formed at the walls.

The DMPC vesicles transitioned from nodal focusing to anti-nodal focusing at 23.2° C., which is around its melting point. Because the lipid was pure, no ripple phase was observed and the transition was sudden and highly reproducible. At that temperature, which is in the middle of the expected operational range, the stiffness of the vesicle was approximately 1 kPa. A plot of the stiffness versus $T_{cp}$ ($T_\Phi$) can be plotted for pure lipids, binary lipid mixtures, and lipids with sterol (e.g., cholesterol), and the relationship fit can be assessed to determine its statistical significance.

Based on that, the limits of the stiffness can be determined, assuming that lipids and sterols are the main determinants for this transition.

EXAMPLE 6

Evaluation of Sensitivity and Efficiency of Thermo-Acoustofluidic Separation of Vesicles To evaluate the sensitivity of thermo-acoustophoresis, vesicles with closely matched $T_\Phi$ values (as close as 0.2° C.) can be evaluated over the whole range of useful temperatures for the vesicles. It is believed that the sensitivity may be less than 1° C., but various sensitivity values can be expected, depending on the range of $T_\Phi$ of the vesicles (i.e., lower sensitivity in 10.1-20° C. than in 20.1° C.-30° C., or vice).

The separation efficiency depends on the purity of each of the streams in the microfluidic device. The microfluidic main channel can splits into three channels, two at each of the walls and one at the center. One aim is to recover with the least disturbance each of the focus streams of the type shown in FIG. 5B. However, this recovery may be affected by various factors such as (1) unresponsive cells/vesicles, (2) slow-responsive cells/vesicles, (3) turbulence in the channel or at the split, and (4) change in acoustic standing-wave along the length of the microchannel. Therefore, the separation efficiency can be evaluated following the equations for the example of DMPC and DPPC:

$R_{DMPC} = C_{DMPC}/(C_{DMPC})_0$: Recovery of DMPC $R_{DPPC} = C_{DPPC}/(C_{DPPC})_0$: Recovery of DPPC $S_{DMPC,DPPC} = R_{DMPC}/R_{DPPC}$: Separation factor (3)

The recovery can be dependent on the sensitivity can be thoroughly investigated using both an approach as shown in FIG. 5C and the equations of Equation Set (3). Any discrepancy between the values may imply fluid dynamic disturbances, which may require redesigning the microchannel for possibly narrower microchannel to reduce the Reynolds number to <10 to minimize turbulence, and thus reduce mixing.

EXAMPLE 7

Effect of Cholesterol Content on Separation of Vesicles

Vesicles with various contents of cholesterol, up to C/PL=0.3 were synthesized to investigate the effect of effect of C/PL on $T_\Phi$. Each vesicle suspension was injected into the microfluidic channel while the signal generator was set to the first harmonic frequency determined prior to the experiments using initial conditions. A prompt focusing response of vesicles to the nodal region was then observed. A controllable temperature increase was then initiated while the vesicles were visually monitored under a fluorescence microscope.

The temperature at which the vesicles initiated their migration towards the anti-nodal regions (the walls in a first harmonic channel) was recorded as the $T_\Phi$ of that particular vesicles composition. In all systems, only a single point is identified as the $T_\Phi$ during the heating experiment. However, temperatures recorded as the $T_\Phi$ on heating differed slightly with the ones observed during cooling. This difference, which was likely due to the heat capacity in the vesicles, was less than 2° C. (at heating/cooling rates of 5° C./min) and was further minimized by slowing down the temperature cooling sweep to less than 0.5° C. (at heating/cooling rates of 0.5° C./min). The temperature sweep was coupled with a frequency sweep to adjust for the medium's property changes and maintain first harmonic frequency conditions.

Figures 13A, 13B, 13C:
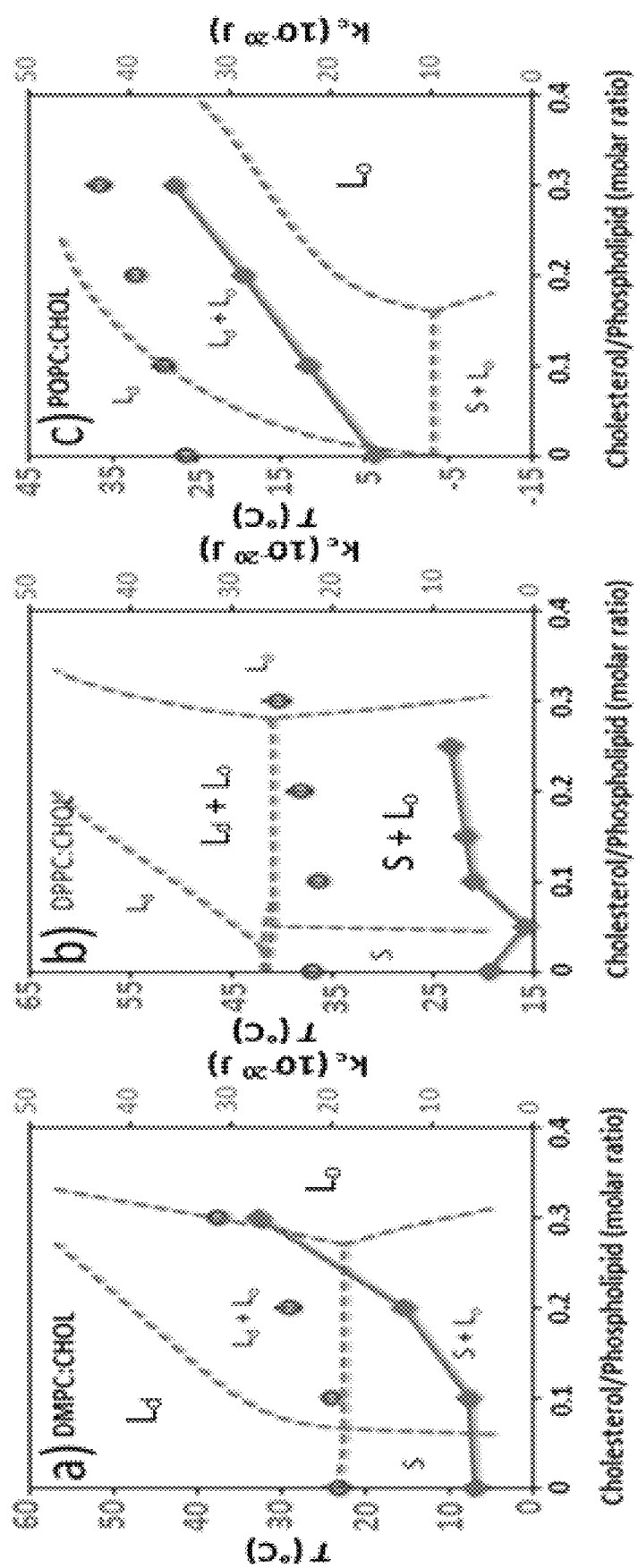
FIGS. 13A, 13B, and 13C illustrate the relationship between acoustic contrast temperature, $T_\Phi$ (circles), vs. C/PL for the binary PC:Chol system comprising DMPC:Chol, DPPC:Chol, and POPC:Chol, respectively. The background dashed lines represent the binary equilibrium phase diagram of the respective system, plotted using the data available in the related art from differential scanning calorimetry, X-ray diffraction, NMR spectroscopies and spin-label ESR spectroscopy studies and statistical thermodynamic calculations. S denotes solid, $L_o$ liquid ordered, and $L_d$ liquid disordered phases. Diamond markers represent the bending stiffness modulus, $k_c$, at specific C/PL at room temperature obtained from X-ray scattering methods and molecular dynamics simulations.

The $T_\Phi$ values recorded in FIGS. 13A-13C are averages of at least five separate vesicle batches. The trend of the change of $T_\Phi$ with C/PL was consistently positive as can be observed in FIGS. 13A-13C. This trend was also consistent with the $k_c$ vs C/PL trend reported in related art. It is evident from the plots that the addition of cholesterol to up to C/PL=0.3 in DMPC vesicles significantly increased the bending rigidity of the membrane. This effect is less apparent for DPPC, which has longer chain length than DPPC. The decrease in the stiffness at low cholesterol concentrations was likely due to the fluidization of the membrane at those concentrations, since cholesterol was shown to disrupt the long-range lateral order of the membrane. For POPC, however, with one mono-unsaturated lipid chain, cholesterol has a rigidifying effect on the membrane, but not as pronounced, as its effect on DMPC and DPPC. This is not surprising as the effect of cholesterol on the membrane's mechanical properties has been shown to be specific to the lipid type.

The $T_\Phi$, in all cases, does not exactly correspond to a distinct phase transition, rather a specific point at which the compressibility of the vesicles reaches a value that would make the $\Phi$ of the suspension lower than zero. In other words, the thermotropic changes in bending stiffness that render the vesicles as roughly as compressible as water do not necessarily lead to a negative $\Phi$ at any point close to the actual temperature of the phase transitions. Such is the case for the POPC:Chol system, in which the main thermotropic transition occurs at a subzero temperature, but its reducing effect on the stiffness becomes evident at a higher temperature. It was confirmed however that the observed $\Phi$ sign change in all the cases is a direct outcome of a phase transition(s) in the membrane of the vesicles.

EXAMPLE 8

Determination of $T_\Phi$ of a Ternary Vesicle System

Membranes composed of more than two PLs are more common in nature. In such systems the C/PL may have competing effects on the membrane stiffness, depending on the type of PLs involved. In order to investigate the effect of cholesterol on $T_\Phi$ of a DMPC:DPPC system, an experiment of 45 individual compositions of DMPC:DPPC:Chol vesicles were prepared using methods provided herein.

Figure 14:
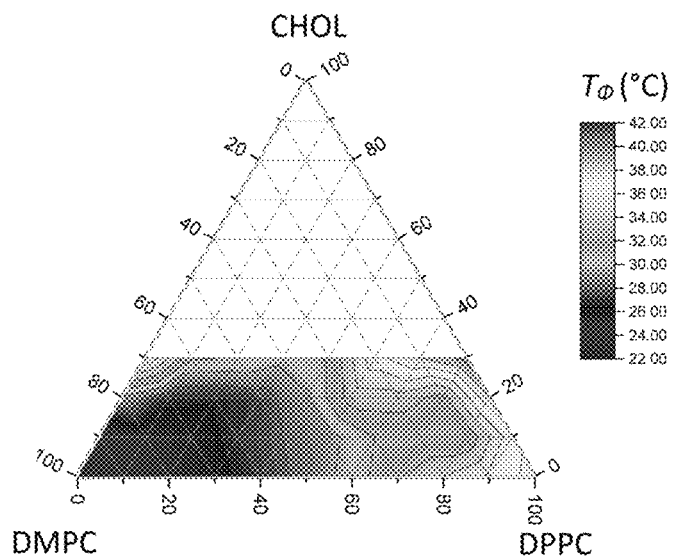
FIG. 14 is a triangular contour map of the measured $T_\Phi$ for the DMPC:DPPC:Chol system up to when C/PL=0.3. The colored surface indicating the value of $T_\Phi$ was obtained using the data of 45 different points across the region of interest by thermo-acoustophoretic heating experiments. Black lines that appear at every fifth contour line mark a temperature difference of 1.5° C. The overall trend in the diagram exhibits an increase in the $T_\Phi$ from the minimum in the region shaded purple to the maximum in either the binary DMPC:Chol (70:30) or the DPPC:Chol (70:30) system.

Using the individual $T_\Phi$ values for each composition measured using the microfluidic device, the contour plot shown in FIG. 14 was developed. Analogous to the binary mixtures, a single point was identified in all cases as the acoustic contrast temperature of the vesicles in a heating experiment. Furthermore, there existed a difference between the temperature registered as the $T_\Phi$ on heating and the one observed during cooling, which did not exceed 2° C. and could be minimized by slowing down the temperature sweep. Referring to FIG. 14, it is shown that along the DMPC:DPPC binary axis, the measured $T_\Phi$ slopes gradually increase from the minimum point of 23.2° C. for the pure DMPC up to 37.6° C. for the pure DPPC. This is, in fact, the overall trend of the diagram especially at the base of the triangle where cholesterol content does not exceed 20%. For the binary DMPC-cholesterol system, $T_\Phi$ shows a sharp increase from the minimum point of 23.2° C. for pure DMPC up to 37.8° C. for the system with 30% cholesterol. On adding DPPC to the binary mixtures, the same trend but with less intensity is observed for the ternary compositions for up to around 60% of DPPC. For ternary compositions with more than 60% DPPC, the changes in $T_\Phi$ is consistent with the decreasing trend observed for the binary DPPC:Chol system, in which $T_\Phi$ first decreases upon addition of cholesterol and then slightly increases up to the maximum value of 40.5° C. for pure DPPC.

Finally, in vesicles with more complex membranes, despite the normally non-uniform mixing of the membrane components, a single T can be identified as the $T_\Phi$. The mapping of $T_\Phi$ affords the opportunity to evaluate the feasibility of a separation system comprising ternary vesicles with various compositions as described herein.

EXAMPLE 9

Study of Thermo-Acoustofluidic Separation in Ternary Vesicle Systems

Because vesicle systems having different C/PL ratios exhibit different $T_\Phi$ values, the thermo-acoustofluidic separation of these vesicles can be accomplished. In order to determine the temperature at which the acoustophoresis can occur, the calculated $\Phi$ of each of the vesicles was plotted against temperature in FIGS. 15A and 15B. The intercept with the abscissa in each vesicle system denote the temperature at which $\Phi=0$, also defined as $T_\Phi$.

Figure 15A:
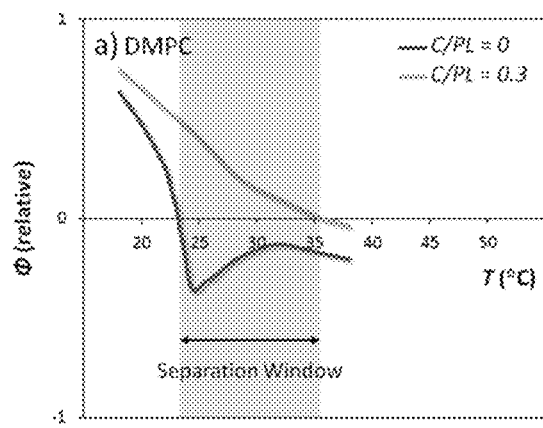
FIGS. 15A and 15B demonstrate the relative values of $\Phi$ for DMPC and DPPC vesicles, respectively, in pure state and in C/PL=0.3. The temperature windows are shaded and are considered the temperature range within which separation could be achieved due to the opposite directions of migration of the vesicles. The relative values of $\Phi$ were calculated using vesicle compressibility data reported in the related art.
Figure 15B:
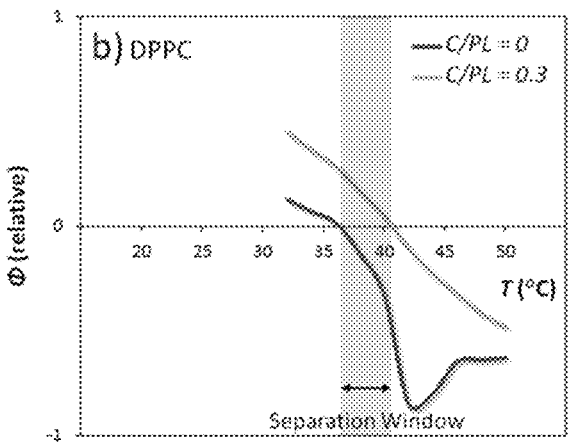

In FIG. 15A, the range of temperatures between the $T_\Phi$ of C/PL=0 and the $T_\Phi$ of C/PL=0.3 can be considered as the separation "window" for the acoustophoresis. This means that a separation temperature set within this window would cause the migration of vesicles in opposite directions (i.e., wall and center), thus yielding a separation. The window was 13.4° C. wide for DMPC:Chol and 3.9° C. wide for DPPC:Chol systems. The widths of the windows were significantly different considering that both systems were composed for C/PL=0 and C/PL=0.3. However, the effect of cholesterol content on each of the PCs yielded a different degree of stiffness change as discussed earlier.

EXAMPLE 10

Multi-Stage Separation of Vesicles

To examine the feasibility of the separation of more than two vesicle systems via thermo-acoustophoresis, vesicles with distinct membrane compositions were prepared and examined in a multi-stage device (FIGS. 16A-16E).

Figure 16A:
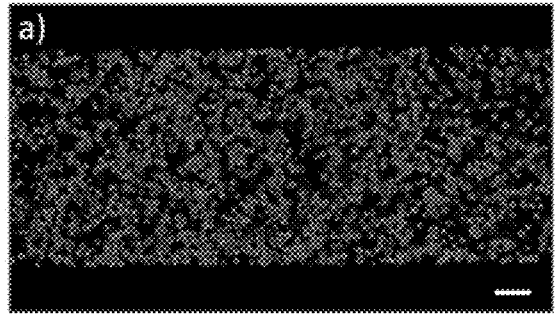
FIG. 16A is a channel view fluorescence micrograph of randomly dispersed vesicles of C/PL=0.1 (green), C/PL=0.2 (red), and C/PL=0.3 (blue) at T=23° C. when the Peltier element and the actuators were switched off.

The selected compositions were 0.1 C/PL, 0.2 C/PL, and 0.3 C/PL, which were fluorescently tagged with green, red, and blue dye, respectively. In all cases, the total lipid used in the preparation of the vesicles was about 2 wt %, yielding vesicles with an average diameter of approximately 12 µm. The $T_\Phi$ for these compositions was pre-measured as 24.2° C. for C/PL=0.1, 29.2° C. for C/PL=0.2, and 37.8° C. for C/PL=0.3. Since the layout of the channel schematically shown in FIG. 16C was modified to accommodate multi-stage separations, the new microfluidic device employed two Peltier elements and two actuators positioned under the main channel preceding the splits. The second actuator was used when necessary to accommodate for the temperature-induced changes in the first harmonic frequency. When both Peltier elements and actuators are switched off (T=23° C.), all vesicles were randomly dispersed (FIG. 16A).

Figure 16B:
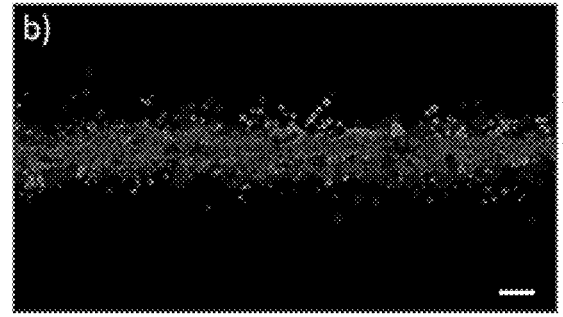
FIG. 16B is a fluorescence micrograph showing all vesicles focusing on the nodal region when the actuators are switched on to first harmonic frequency with Peltier elements remaining off
Figure 16C:
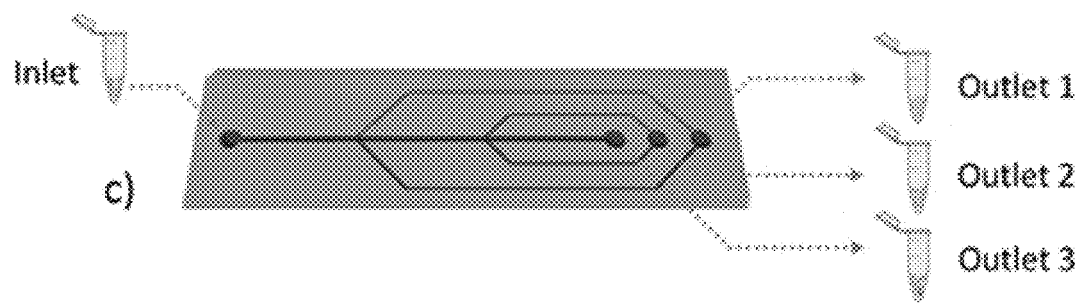
FIG. 16C is a schematic of the multi-stage separation channel showing the inlet and 3 outlets.
Figure 16D:
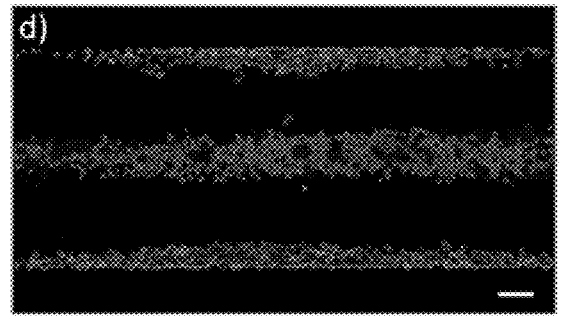
FIG. 16D is a fluorescence micrograph showing the C/PL=0.1 vesicles migrating to the anti-nodal zones when the first stage channel temperature was set to 27° C.

Upon actuation of the first transducer (f=1.33 MHz, 50 Vpp) at the same temperature, all vesicles swiftly migrated toward the central region of the channel, i.e., the node (FIG. 16B). As the separation temperature was below all $T_\Phi$ values for the various compositions, the nodal migration was expected. After the first Peltier element was switched on and the first stage channel reached a temperature of ~27° C., the separation temperature exceeded the $T_\Phi$ of the C/PL=0.1 while remained lower than the $T_\Phi$ of both C/PL=0.2 and 0.3. Under these conditions, C/PL=0.2 and 0.3 vesicles remained well-focused at the node in the center of the channel, while C/PL=0.1 vesicles migrated towards the walls (FIG. 16D). These vesicles were gradually collected from the first outlet while the remaining vesicles proceeded to the second stage of the separation.

Figure 16E:
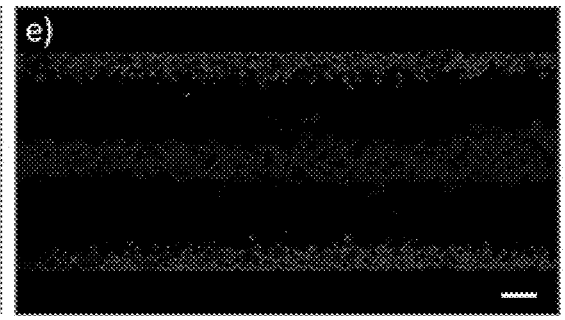
FIG. 16E is a fluorescence micrograph showing the C/PL=0.2 vesicles migrating to the anti-nodal zones when the first stage channel temperature was set to 31° C. All fluorescence micrographs have a scale bar of 80 μM.

At the second stage of the separation the Peltier element was set to achieve an average second stage channel temperature of ~31° C. at the given conditions, while the second actuator was set to f=1.46 MHz, 50 Vpp. Under these conditions the separation temperature exceeding the $T_\Phi$ of the C/PL=0.2 while remaining lower than the $T_\Phi$ of the C/PL=0.3; therefore, the C/PL=0.2 vesicles migrated towards to the walls while the C/PL=0.3 vesicles remained focused at the center (FIG. 16E). The wall focused vesicles in the second stage were collected from outlet 2, while the second stage main channel vesicles were collected from outlet 3.

EXAMPLE 11

Efficiency of Multi-Stage Vesicle Separation

The efficiency of the separation was dependent on many parameters out of which only the temperatures of the first and second stages of the separation was varied while the rest were maintained constant. The vesicles in each of the injected samples included equal counts of each of the three compositions of vesicles to minimize concentration-caused disturbances. Mixtures were prepared immediately before the separation experiments to minimize the exchange of cholesterol between the various C/PL vesicles. The flow rate remained constant during all experiments at a rate of 5 µL/min.

Figure 17:
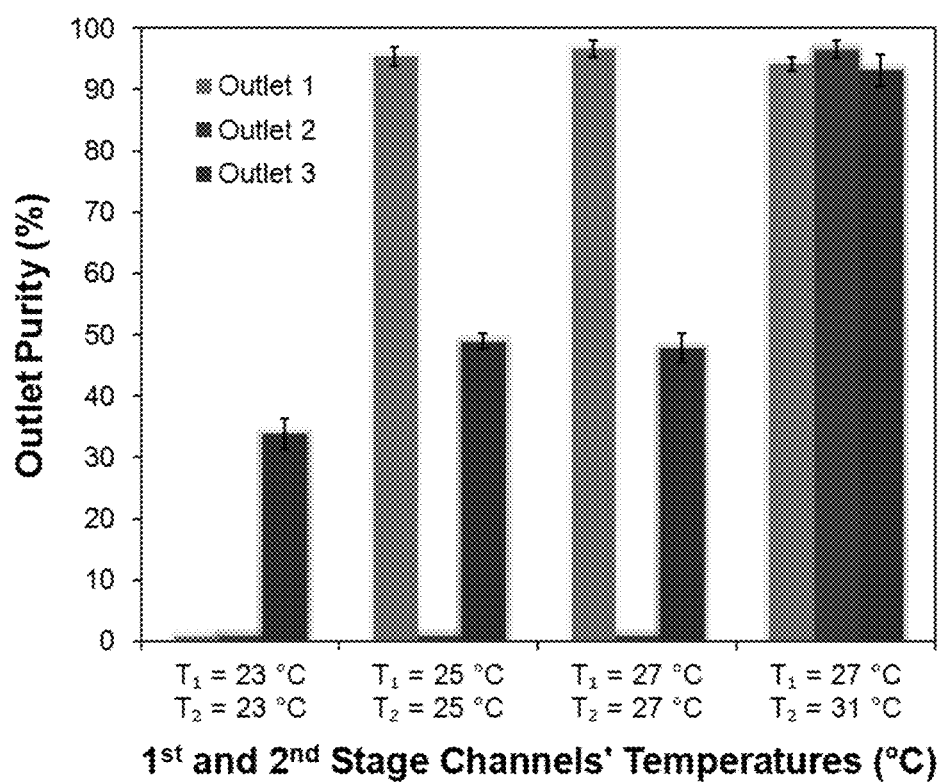
FIG. 17 demonstrates the purity of collected vesicle samples from outlets 1, 2, and 3 at various temperature conditions of the two stages of the separation. Purities were quantified based on the intended vesicle for each outlet with C/PL=0.1 in outlet 1, C/PL=0.2 in outlet 2, and C/PL=0.3 in outlet 3.

In order to study the effect of temperatures on the separation efficiency, four different experiments were designed using identical vesicles mixtures of C/PL=0.1, 0.2, and 0.3 in equal counts pre-labelled with green, red, and blue fluorescent tags, respectively. The temperatures of the two stages of the separation were considered $T_1$ for stage one and $T_2$ for stage two and were controlled by two Peltier elements while holding all other parameters virtually constant. The efficiency of the separation was assessed by measuring the percentage of C/PL=0.1 vesicles in outlets 1, C/PL=0.2 vesicles in outlet 2, and C/PL=0.3 vesicles in outlet 3 using fluorescence signals. These values are summarized in the bar graph in FIG. 17.

When both stages were set to 23° C. (room temperature), all three vesicles were nodally focused and no vesicles were collected in outlets 1 and 2. This caused all three types of vesicles to exit from outlet 3, leading to an outlet 3 purity of 33.9%. When both stages' temperatures were increased to 25° C., the first stage separation operated efficiently since the separation temperature exceeded the $T_\Phi$ of C/PL=0.1 vesicles and thus a purity in outlet 1 of 95.4% was achieved. The second stage separation did not operate efficiently however, and both vesicles were nodally focused and exited from outlet 3 causing outlet 3 purity to be 49.0%. When both stages were raised to 27° C. the same behavior was observed since the second stage temperature did not exceed the $T_\Phi$ of the C/PL=0.2 vesicles of 29.2° C. However, when the second stage temperature was increased to 31° C. both stages of the separation operated efficiently and purities reached 94.2%, 96.5%, and 93.1% for outlets 1, 2, and 3, respectively. The conditions of these two stages of separation were identical to the conditions shown in FIGS. 16D and 16E. These results confirm that thermo-acoustophoresis is a temperature-enabled separation that unless properly designed, simple acoustophoresis would not yield such separation.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Alberts, B.; Johnson, A.; Lewis, J.; Morgan, D.; Raff, M.; Roberts, K.; Walter, P. Molecular Biology of the Cell, 6th ed.; Garland Science, 2014.

2. Phillip, J. M.; Aifuwa, I.; Walston, J.; Wirtz, D. Annu. Rev. Biomed. Eng. 2015, 17, 113. (b) Schulze, C.; Wetzel, F.; Kueper, T.; Malsen, A.; Muhr, G.; Jaspers, S.; Blatt, T.; Wittern, K. P.; Wenck, H.; Käs, J. A. Clin. Plast. Surg. 2010, 39 (1), 9.

3. Lee, G. Y. H.; Lim, C. T. Trends Biotechnol. 2007, 25 (3), 111.

4. Lam, W. a; Rosenbluth, M. J.; Fletcher, D. a; Dc, W. 2007, 109 (8), 3505.

5. Di Carlo, D. J. Lab. Autom. 2012, 17 (1), 32. (b) Suresh, S. Acta Mater. 2007, 55 (12), 3989.

6. Suwanarusk, R.; Cooke, B. M.; Dondorp, A. M.; Silamut, K.; Sattabongkot, J.; White, N. J.; Udomsangpetch, R. J. Infect. Dis. 2004, 189 (2), 190.

7. Nash, G. B.; Johnson, C. S.; Meiselman, H. J. Blood 1984, 63 (1), 73.

8. Bruus, H. Lab Chip 2012, 12 (6), 1014.

9. Heimburg, T. Biochim. Biophys. Acta-Biomembr. 1998, 1415 (1), 147. (b) Heimburg, T. Thermal Biophysics of Membranes; WILEY-VCH Verlag GmbH & Co. KGaA, Weinheim, 2007. (c) Halstenberg, S.; Heimburg, T.; Hianik, T.; Kaatze, U.; Krivanek, R. Biophys J 1998, 75 (1), 264. (d) Krivanek, R.; Rybar, P.; Prenner, E. J.; McElhaney, R. N.; Hianik, T. Biochim. Biophys. Acta-Biomembr. 2001, 1510 (1-2), 452. (e) Needham, D.; Evans, E. Biochemistry 1988, 27 (21), 8261. (f) Schrader, W.; Ebel, H.; Grabitz, P.; Hanke, E.; Heimburg, T.; Hoeckel, M.; Kahle, M.; Wente, F.; Kaatze, U. J. Phys. Chem. B 2002, 106 (25), 10. Laurell, T.; Petersson, F.; Nilsson, A. Chem. Soc. Rev. 2007, 36 (3), 492. (b) Wood, C. D.; Evans, S. D.; Cunningham, J. E.; O'Rorke, R.; Walti, C.; Davies, A. G. Appl. Phys. Lett. 2008, 92 (4), 10.

11. Li, P.; Mao, Z.; Peng, Z.; Zhou, L.; Chen, Y.; Huang, P.-H.; Truica, C. I.; Drabick, J. J.; El-Deiry, W. S.; Dao, M.; Suresh, S.; Huang, T. J. Proc. Natl. Acad. Sci. U.S.A 2015, 112 (16), 4970. (b) Yang, A. H. J.; Soh, H. T. Anal. Chem. 2012, 84, 10756. (c) Grenvall, C.; Magnusson, C.; Lilja, H.; Laurell, T. Anal. Chem. 2015, 5596. (d) Thévoz, P.; Adams, J. D.; Shea, H.; Bruus, H.; Soh, H. T. Anal. Chem. 2010, 82 (7), 3094.

12. Faria, E. C.; Ma, N.; Gazi, E.; Gardner, P.; Brown, M.; Clarke, N. W.; Snook, R. D. Analyst 2008, 133 (11), 1498.

13. Thévoz, P.; Adams, J. D.; Shea, H.; Bruus, H.; Soh, H. T. Anal. Chem. 2010, 82 (7), 3094.

14. Burguillos, M. a.; Magnusson, C.; Nordin, M.; Lenshof, A.; Augustsson, P.; Hansson, M. J.; Elmér, E.; Lilja, H.; Brundin, P.; Laurell, T.; Deierborg, T. PLoS One 2013, 8 (5), 1.

15. Yang, A. H. J.; Soh, H. T. Anal. Chem. 2012, 84, 10756.

16. Grenvall, C.; Magnusson, C.; Lilja, H.; Laurell, T. Anal. Chem. 2015, 150513092215004.

17. Ward, M.; Turner, P.; DeJohn, M.; Kaduchak, G. Curr. Protoc. Cytom. 2009, No. SUPPL. 49, 1.

18. Walde, P.; Cosentino, K.; Engel, H.; Stano, P. ChemBioChem 2010, 11 (7), 848.

19. Mabrey, S.; Sturtevant, J. M. Proc. Natl. Acad. Sci. U.S.A 1976, 73 (11), 3862. (b) Cheng, W. H. Biochim. Biophys. Acta 1980, 600 (2), 358. (c) Shimshick, E. J.; McConnell, H. M. Biochemistry 1973, 12 (12), 2351. (d) Van Dijck, P. W. M.; Kaper, A. J.; Oonk, H. A. J.; De Gier, J. BBA-Biomembr. 1977, 470 (1), 58.

20. Dimova, R.; Pouligny, B.; Dietrich, C. Biophys. J. 2000, 79 (1), 340. (b) Seto, H.; Yamada, N. L.; Nagao, M.; Hishida, M.; Takeda, T. Eur. Phys. J. E. Soft Matter 2008, 26 (1-2), 217. (c) Yi, Z.; Nagao, M.; Bossev, D. P. J. Phys. Condens. Matter 2009, 21 (15), 155104. (d) Woodka, A. C.; Butler, P. D.; Porcar, L.; Farago, B.; Nagao, M. Phys. Rev. Lett. 2012, 109 (5), 058102.

21. Marsh, D. Handbook of Lipid Bilayers, 2nd ed.; CRC Press, Taylor & Francis Group, LLC, 2013.

22. Prabhune, M., G. Beige, A. Dotzauer, J. Bullerdiek and M. Radmacher, Comparison of Mechanical Properties of Normal and Malignant Thyroid Cells. Micron, 2012. 43(12): p. 1267-1272.

23. Xu, W. W., R. Mezencev, B. Kim, L. J. Wang, J. McDonald and T. Sulchek, Cell Stiffness Is a Biomarker of the Metastatic Potential of Ovarian Cancer Cells. Plos One, 2012. 7(10).

24. Li, Q. S., G. Y. H. Lee, C. N. Ong and C. T. Lim, Afm Indentation Study of Breast Cancer Cells.

25. Biochemical and Biophysical Research Communications, 2008. 374(4): p. 609-613.

26. Hou, H. W., Q. S. Li, G. Y. H. Lee, A. P. Kumar, C. N. Ong and C. T. Lim, Deformability Study of Breast Cancer Cells Using Microfluidics. Biomedical Microdevices, 2009. 11(3): p. 557-564, 27. Swaminathan, V., K. Mythreye, E. T. O'Brien, A. Berchuck, G. C. Blobe and R. Superfine, Mechanical Stiffness Grades Metastatic Potential in Patient Tumor Cells and in Cancer Cell Lines. Cancer Research, 2011. 71(15): p. 5075-5080.

28. Hosseini, S. M. and J. J. Feng, How Malaria Parasites Reduce the Deformability of Infected Red Blood Cells. Biophysical Journal, 2012. 103(1): p. 1-10.

29. Guo, Q., S. J. Reiling, P. Rohrbach and H. S. Ma, Microfluidic Biomechanical Assay for Red Blood Cells Parasitized by *Plasmodium Falciparum*. Lab on a Chip, 2012. 12(6): p. 1143-1150.

30. Aingaran, M., R. Zhang, S. K. Law, Z. L. Peng, A. Undisz, E. Meyer, M. Diez-Silva, T. A. Burke, T. Spielmann, C. T. Lim, S. Suresh, M. Dao and M. Marti, Ty Host Cell Deformability Is Linked to Transmission in the Human 31. Wang, J. C., M. S. Turner, G. Agarwal, S. Kwong, R. Josephs, F. A. Ferrone and R. W. Briehl, Micromechanics of Isolated Sickle Cell Hemoglobin Fibers: Bending Moduli and Persistence Lengths. J. Mol. Biol., 2002. 315(Copyright (C) 2015 American Chemical Society (ACS). All Rights Reserved.): p. 601-612.

32. Wandersee, N. J., J. L. Maciaszek, K. M. Giger, M. S. Hanson, S. Zheng, Y. Guo, B. Mickelson, C. A. Hillery, G. Lykotrafitis, P. S. Low and N. Hogg, Dietary Supplementation with Docosahexanoic Acid (Dha) Increases Red Blood Cell Membrane Flexibility in Mice with Sickle Cell Disease. Blood Cells, Mol., Dis., 2015. 54(Copyright (C) 2015 American Chemical Society (ACS). All Rights Reserved.): p. 183-188.

33. Moessmer, G. and H. J. Meiselman, A New Micropore Filtration Approach to the Analysis of White Cell Rheology. Biorheology, 1990. 27(6): p. 829-848.

34. Shelby, J. P., J. White, K. Ganesan, P. K. Rathod and D. T. Chiu, A Microfluidic Model for Single-Cell Capillary Obstruction by *Plasmodium Falciparum* Infected Erythrocytes. Proceedings of the National Academy of Sciences of the United States of America, 2003. 100(25): p. 14618-14622.

35. Altschuler, S. J. and L. F. Wu, Cellular Heterogeneity: Do Differences Make a Difference? Cell. 141(4): p. 559-563.

36. Chiou, Y. W., H. K. Lin, M. J. Tang, H. H. Lin and M. L. Yeh, The Influence of Physical and Physiological Cues on Atomic Force Microscopy-Based Cell Stiffness Assessment. PLoS One, 2013. 8(10).

37. Thomas, G., N. A. Burnham, T. A. Camesano and Q. Wen, Measuring the Mechanical Properties of Living Cells Using Atomic Force Microscopy. Jove-Journal of Visualized Experiments, 2013(76).

38. Vichare, S., M. M. Inamdar and S. Sen, Influence of Cell Spreading and Contractility on Stiffness Measurements Using Afm. Soft Matter, 2012. 8(40): p. 10464-10471.

39. Zhou, Z. L., T. H. Hui, B. Tang and A. M. W. Ngan, Accurate Measurement of Stiffness of Leukemia Cells and Leukocytes Using an Optical Trap by a Rate-Jump Method. Rsc Advances, 2014. 4(17): p. 8453-8460.

40. Shen, Y. J., M. Nakajima, Z. Yang, H. Tajima, Z. Najdovski, M. Homma and T. Fukuda, Single Cell Stiffness Measurement at Various Humidity Conditions by Nanomanipulation of a Nano-Needle. Nanotechnology, 2013. 24(14).

41. Nematbakhsh, Y. and C. T. Lim, Cell Biomechanics and Its Applications in Human Disease Diagnosis. Acta Mechanica Sinica, 2015. 31(2): p. 268-273.

42. Guz, N., M. Dokukin, V. Kalaparthi and I. Sokolov, If Cell Mechanics Can Be Described by Elastic Modulus: Study of Different Models and Probes Used in Indentation Experiments. Biophysical Journal, 2014. 107(3): p. 564-575.

43. Lekka, M., K. Pogoda, J. Gostek, O. Klymenko, S. Prauzner-Bechcicki, J. Wiltowska-Zuber, J. Jaczewska, J. Lekki and Z. Stachura, Cancer Cell Recognition-Mechanical Phenotype. Micron, 2012. 43(12): p. 1259-1266.

44. Lekka, M., D. Gil, K. Pogoda, J. Dulinska-Litewka, R. Jach, J. Gostek, O. Klymenko, S. Prauzner-Bechcicki, Z. Stachura, J. Wiltowska-Zuber, K. Okon and P. Laidler, Cancer Cell Detection in Tissue Sections Using Afm. Archives of Biochemistry and Biophysics, 2012. 518(2): p. 151-156.

45. Lee, P. H. Wu, J. R. Staunton, R. Ros, G. D. Longmore and D. Wirtz, Mismatch in Mechanical and Adhesive Properties Induces Pulsating Cancer Cell Migration in Epithelial Monolayer. Biophysical Journal, 2012. 102(12): p. 2731-2741.

46. Faria, E. C., N. Ma, E. Gazi, P. Gardner, M. Brown, N. W. Clarke and R. D. Snooka, Measurement of Elastic Properties of Prostate Cancer Cells Using Afm. Analyst, 2008. 133(11): p. 1498-1500.

47. Kamakura, I., K. Yasuda and Y. Kumamoto, Unified Description of Second-Order Phenomena in Sound Waves. Electronics and Communications in Japan Part Iii-Fundamental Electronic Science, 1999. 82(2): p. 76-82.

48. Kapishnikov, S., V. Kantsler and V. Steinberg, Continuous Particle Size Separation and Size Sorting Using Ultrasound in a Microchannel. Journal of Statistical Mechanics-Theory and Experiment, 2006.

49. Walde, P., K. Cosentino, H. Engel and P. Stano, Giant Vesicles: Preparations and Applications. Chembiochem, 2010. 11(7): p. 848-865.

50. Pons, M., M. Foradada and J. Estelrich, Liposomes Obtained by the Ethanol Injection Method. International Journal of Pharmaceutics, 1993. 95(1-3): p. 51-56.

51. G. Pabst, N. Kučerka, M.-P. Nieh and J. Katsaras, Eds., *Liposomes, Lipid Bilayers and Model Membranes From Basic Research to Application*, CRC Press, Taylor & Francis Group, LLC, Boca Raton, Fla., 2014.

52. Robert B. Gennis, *Biomembranes: Molecular Structure and Function*, Springer-Verlag New York, 1st edn., 1989.

53. Shu Chien, *Annu. Rev. Physiol.*, 1987, 49, 177-192.

54. A. Schaefer and P. L. Hordijk, *J. Cell Sci.*, 2015, 128, 2221-30.

55. D. Di Carlo, *J. Lab. Autom.*, 2012, 17, 32-42.

56. I. Nakazawa and M. Iwaizumi, *Tohoku J. Exp. Med.*, 1989, 157, 193-198.

57. V. Swaminathan, K. Mythreye, E. Tim O'Brien, A. Berchuck, G. C. Blobe and R. Superfine, *Cancer Res.*, 2011, 71, 5075-5080.

58. W. Xu, R. Mezencev, B. Kim, L. Wang, J. McDonald and I. Sulchek, *PLoS One*, 2012, 7, e46609.

59. J. Fenner, A. C. Stacer, F. Winterroth, T. D. Johnson, K. E. Luker and G. D. Luker, *Sci. Rep.*, 2014, 4, 5512.

60. R. Suwanarusk, B. M. Cooke, A. M. Dondorp, K. Silamut, J. Sattabongkot, N. J. White and R. Udomsangpetch, *J. Infect. Dis.*, 2004, 189, 190-194.

61. G. a Barabino, M. O. Platt and D. K. Kaul, *Annu. Rev. Biomed. Eng.*, 2010, 12, 345-367.

62. E. C. Faria, N. Ma, E. Gazi, P. Gardner, M. Brown, N. W. Clarke and R. D. Snook, *Analyst*, 2008, 133, 1498-1500.

63. T. Heimburg, *Thermal Biophysics of Membranes*, WILEY-VCH Verlag GmbH & Co. KGaA, Weinheim, Germany, 2007.

64. H. T. Tien and A. Ottova-Leitmannova, *Membrane Biophysics: As Viewed from Experimental Bilayer Lipid Membranes*, Elsevier Science B. V., Amsterdam, 1st edn., 2000.

65. B. Alberts, A. Johnson, J. Lewis, D. Morgan, M. Raff, K. Roberts and P. Walter, *Molecular Biology of the Cell*, Garland Science, 6th edn., 2014.

66. R. Phillips, J. Kondev, J. Theriot and H. G. Garcia, *Physical Biology of the Cell*, Garland Science, Taylor & Francis Group, LLC, New York, N.Y., 2nd edn., 2013.

67. D. N. Tziakas, J. C. Kaski, G. K. Chalikias, C. Romero, S. Fredericks, I. K. Tentes, A. X. Kortsaris, D. I. Hatseras and D. W. Holt, *J. Am. Coll. Cardiol.*, 2007, 49, 2081-2089.

68. R. Jelinek, Ed., *Lipids and Cellular Membranes in Amyloid Diseases*, WILEY-VCH Verlag & Co. KGaA, Weinheim, Germany, 2011.

69. W. I. M. J. Van Blitterswijk, H. Hilkmann and T. Hengeveld, *Biochim. Biophys. Acta*, 1984, 778, 521-529.

70. K. Kojima, *Nagoya J Med Sci*, 1993, 1-18.

71. Y. C. Li, M. J. Park, S.-K. Ye, C.-W. Kim and Y.-N. Kim, *Am. J. Pathol.*, 2006, 168, 1107-1118-1405.

72. M. H. Hager, K. R. Solomon and M. R. Freeman, *Curr. Opin. Clin. Nutr. Metab. Care*, 2006, 9, 379-385.

73. V. a. Cortes, D. Busso, P. Mardones, A. Maiz, A. Arteaga, F. Nervi and A. Rigotti, *Biol. Rev.*, 2013, 88, 825-843.

74. Nicolau C T, T. P, F. M, B. E and T. S, *Sangre* (Barc), 1964, 10, 282-288.

75. C. Allard, N. Mohandas and M. Bessis, in *Red Cell Rheology*, eds. M. Bessis, S. B. Shohet and N. Mohandas, Springer Berlin Heidelberg, Berlin, Heidelberg, 1978, pp. 209-221.

76. S. K. Ballas, J. Lamer, E. D. Smith, S. Surrey, E. Schwartz and E. F. Rappaport, *Blood*, 1988, 72, 1216 LP-1223.

77. M. Bessis and N. Mohandas, *Blood Cells*, 1977, 3, 229-239.

78. W. M. Lande, D. L. Andrews, M. R. Clark, N. V Braham, D. M. Black, S. H. Embury and W. C. Mentzer, *Blood*, 1988, 72, 2056 LP-2059.

79. A. J. Dodds, M. J. Boyd, J. Allen, E. D. Bennett, P. T. Flute and J. A. Dormandy, *Br. Heart 1*, 1980, 44, 508-511.

80. J. Dormandy, M. Boyd and E. Ernst, *Scand. J. Clin. Lab. Invest.*, 1981, 41, 195-198.

81. P. Brown and M. J. G. Flarrison, *Clin. Hemorheol.*, 1989, 9, 139-147.

82. S. Ekeström, B. L. Koul and T. Sonnenfeld, *Scand. J. Thorac. Cardiovasc. Surg.*, 1983, 17, 41-44.

83. T. Hirayama, H. Yamaguchi, M. Allers and D. Roberts, *Scand. J. Thorac. Cardiovasc. Surg.*, 1985, 19, 263-265.

84. T. Hirayama, H. Yamaguchi, M. Allers, D. Roberts and G. William-Olsson, *Scand. J. Thorac. Cardiovasc. Surg.*, 1985, 19, 257-262.

85. D. Bareford, P. C. W. Stone, N. M. Caldwell and J. Stuart, *Clin. Hemorheol.*, 1985, 5, 473-481.

86. D. Bareford, G. S. Lucas, P. C. W. Stone, N. M. Caldwell, R. McGonigle and J. Stuart, *Clin. Hemorheol.*, 1986, 6, 501-510.

87. A. Decamps, M. Zandecki, M. Ribiére, J. Goudemand, M. Dracon, A. Tacquet and A. Cosson, *Scand. J. Clin. Lab. Invest.*, 1981, 41, 177-179.

88. Y. Kikuchi, T. Koyama, Y. Koyama, S. Tozawa, T. Arai, M. Horimoto and Y. Kakiuchi, *Nephron*, 1982, 30, 8-14.

89. W. Inauen, M. Staubli, C. Descoeudres, R. L. Galeazzi and P. W. Straub, *Eur. J. Clin. Invest.*, 1982, 12, 173-176.

90. E. Cecchin, S. De Marchi, G. Panarello and V. De Angelis, *Am. J. Nephrol.*, 1987, 7, 18-21.

91. D. E. McMillan, N. G. Utterback and J. La Puma, *Diabetes*, 1978, 27, 895-901.

92. H. Schmid-Schönbein and E. Volger, *Diabetes*, 1976, 25, 897-902.

93. E. Ernst and A. Matrai, *Diabetes*, 1986, 35, 1412 LP-1415.

94. I. Juhan, P. Vague, M. Buonocore, J. P. Moulin, M. F. Calas, B. Vialettes and J. J. Verdot, *Scand. J. Clin. Lab. Invest.*, 1981, 41, 159-164.

95. I. Juhan, M. Buonocore, R. Jouve, P. Vague, J. P. Moulin and B. Vialettes, *Lancet*, 1982, 319, 535-537.

96. P. Ozanne, C. Le Devehat, D. Boudart, A. Lemoine, R. Leloup and M. Fournier, *Scand. J. Clin. Lab. Invest.*, 1981, 41, 259-260.

97. G. D. O. Lowe, M. M. Drummond, J. J. F. Belch, J. M. Lowe and W. G. MacCuish, A. C., & Manderson, in *Microvascular Research*, Academic Press Inc JNL-COMP Subscriptions, San Diego, Calif., 1979, vol. 17, p. S58.

98. H. A. Cranston, C. W. Boylan, G. L. Carroll, S. P. Sutera, Williamson, I. Y. Gluzman and D. J. Krogstad, *Science* (80-.)., 1984, 223, 400 LP-403.

99. G. Nash, E. O'Brien, E. Gordon-Smith and J. Dormandy, *Blood*, 1989, 74, 855 LP-861.

100. A. H. J. Yang and H. T. Soh, *Anal. Chem.*, 2012, 84, 10756-10762.

101. L. P. Gor'kov, *Sov. Phys. Dokl.*, 1962, 6, 773-775.

102. H. Bruus, *Lab Chip*, 2012, 12, 1014-21.

103. A. Dolatmoradi and B. El-Zahab, *Lab Chip*, 2016, 16, 3449-3453.

104. M. Ward, P. Turner, M. DeJohn and G. Kaduchak, *Curr. Protoc. Cytom.*, 2009, 1-12.

105. F. Petersson, L. Aberg, A. M. Sward-Nilsson and T. Laurell, *Anal. Chem.*, 2007, 79, 5117-5123.

106. A. Lenshof, C. Magnusson and T. Laurell, *Lab Chip*, 2012, 12, 1210.

107. C. W. Shields, L. M. Johnson, L. Gao and G. P. López, *Langmuir*, 2014, 30, 3923-3927.

108. D. Marsh, *Handbook of Lipid Bilayers*, CRC Press, Taylor & Francis Group, LLC, 2nd edn., 2013.

109. R. Dimova, B. Pouligny and C. Dietrich, *Biophys. J.*, 2000, 79, 340-356.

110. Z. Yi, M. Nagao and D. P. Bossev, *J. Phys. Condens. Matter*, 2009, 21, 155104.

111. A. C. Woodka, P. D. Butler, L. Porcar, B. Farago and M. Nagao, *Phys. Rev. Lett.*, 2012, 109, 58102.

112. T. Heimburg and A. D. Jackson, *Proc. Natl. Acad. Sci. U.S.A*, 2005, 102, 9790-9795.

113. M. Tarini, P. Cignoni and C. Montani, *IEEE Trans. Vis. Comput. Graph.*, 2006, 12, 1237-1244.

114. H. Heller, Technical University of Munich, 1993.

115. H. Heller, M. Schaefer and K. Schulten, *J. Phys. Chem.*, 1993, 97, 8343-8360.

116. J. Pan, T. T. Mills, S. Tristram-Nagle and J. F. Nagle, *Phys. Rev. Lett.*, 2008, 100, 1-4.

117. C. Hofsa$\beta$, E. Lindahl and O. Edholm, *Biophys. J.*, 2003, 84, 2192-2206.

118. K. J. Tierney, D. E. Block and M. L. Longo, *Biophys. J*, 2005, 89, 2481-2493.

119. R. S. Gracià, N. Bezlyepkina, R. L. Knorr, R. Lipowsky and R. Dimova, *Soft Matter*, 2010, 6, 1472.

120. P. F. Almeida, W. L. Vaz and T. E. Thompson, *Biochemistry*, 1992, 31, 6739-6747.

121. M. B. Sankaram and T. E. Thompson, *Proc. Natl. Acad. Sci. U S. A.*, 1991, 88, 8686-8690.

122. C. Reyes Mateo, a Ulises Acuña and J. C. Brochon, *Biophys. J.*, 1995, 68, 978-987.

123. S. Halstenberg, I. Heimburg, T. Hianik, U. Kaatze and R. Krivanek, *Biophys J*, 1998, 75, 264-271.

124. R. Krivanek, L. Okoro and R. Winter, *Biophys. J.*, 2008, 94, 3538 48.

What is claimed is:

1. A method of separating vesicles, the method comprising:
providing to a microfluidic device a population of vesicles suspended in an aqueous medium, the vesicles having the same or approximately the same size, shape, and charge but different stiffness due to different compositions;

applying standing-wave acoustic signals to the microfluidic device, the acoustic signals being set to a pre-determined first harmonic frequency of the vesicles suspended in the aqueous medium; and tuning the temperature of the device to separate vesicles based on their directions of migration as a response to the acoustic signals, each vesicle comprising a lipid bilayer membrane and that the compressibility of vesicles changes at a temperature $T_\Phi$ characteristic to the stiffness of said vesicles in the presence of the acoustic field, and the microfluidic device comprising:
  a microfluidic channel etched on a silicon wafer, the channel comprising an inlet and at least one outlet, the inlet and the at least one outlet being controlled by their respective syringe pump for fluid transport, and if more than one outlet is present, the outlets being separated by a thermally insulating material;
  an optically transparent cover slip placed atop the microfluidic channel;
  at least one acoustic transducer bonded to the back of the microfluidic channel and connected to an AC signal generator and if more than one acoustic transducer is present, each transducer being connected to an independent signal generator;
  at least one thermoelectric transducer positioned in thermal contact with the microfluidic channel, the at least one thermoelectric transducer being capable of controlling the temperature of the channel and if more than one thermoelectric transducer is present, each transducer being operated independently; and
  a heat sink disposed underneath the at least one thermoelectric transducer.

2. The method according to claim 1, the vesicles comprising at least one of mammalian cells, yeast cells, fungus cells, bacteria, lipids, liposomes, exosomes, artificial drugs, and gene delivery vehicles.

3. The method according to claim 1, each vesicle further comprising at least one sterol in its membrane.

4. The method according to claim 1, the population comprising vesicles with at least two distinct lipid bilayer membrane compositions.

5. The method according to claim 4, vesicles of a specific composition being separated when the device is tuned to a temperature higher than the $T_\Phi$ of said vesicles but lower than the $T_\Phi$ of vesicles of different compositions in the population.

6. The method according to claim 1, the temperature of the device being tuned by sweeping a range of temperatures.

7. The method according to claim 5, the compressibility of vesicles increasing as the device is tuned to a temperature higher than the $T_\Phi$ of said vesicles, causing said vesicles to migrate to an anti-nodal position with respect to the applied acoustic signals.

8. The method according to claim 1, the lipids being selected from phosphatidylcholines, phosphatidylserines, phosphatidylglycerols, phosphatidylethanolamines, and phosphatidic acids.

9. The method according to claim 8, the lipids being phosphatidylcholines selected from 1,2-dimyristoyl-sn-glycero-3-phosphocholine (DMPC), 1,2-dipalmitoyl-sn-glycero-3-phosphocholine (DPPC), and 2-palmitoyl-2-oleoyl-sn-glycero-3-phosphocholine (POPC).

10. The method according to claim 1, the thermoelectric transducer being a Peltier element.

11. The method according claim 1, the heat sink being an aluminum plate.

12. The method according to claim 1, said method further comprising collecting separated vesicles from the at least one outlet of the microfluidic channel following temperature tuning.

13. A method of separating vesicles, the method comprising:
providing a microfluidic device for separating vesicles, the device comprising:
  a microfluidic channel etched on a silicon wafer, the channel comprising inlet and at least one outlet, the inlet and the at least one outlet being controlled by their respective syringe pump for fluid transport, and if more than one outlet is present, the outlets being separated by a thermally insulating material;
  an optically transparent cover slip placed atop the microfluidic channel;
  at least one acoustic transducer bonded to the back of the microfluidic channel and connected to an AC signal generator, and if more than one acoustic transducer is present, each transducer being connected to an independent signal generator;
  at least one thermoelectric transducer positioned in thermal contact with the microfluidic channel, the at least one thermoelectric transducer being capable of controlling the temperature of the channel, and if more than one thermoelectric transducer is present, each transducer being, operated independently; and
  an aluminum heat sink disposed underneath the at least one thermoelectric transducer;
providing a population of vesicles suspended in an aqueous medium into the inlet of the device using a syringe pump operating in injection mode, the vesicles having the same or approximately the same size, shape, and charge but at least two distinctly different membrane compositions;
applying to the device standing-wave acoustic signals via a first transducer, the acoustic signals being set to a pre-determined first harmonic frequency of the vesicles suspended in the aqueous medium;
tuning the temperature within the channel by controlling a first Peltier element to separate vesicles based on their directions of migration as a response to the acoustic signals;
collecting the separated vesicles from the channel using a syringe pump operating in withdrawal mode from a first outlet; and
repeating said process until all vesicles are separated,
each vesicle comprising a lipid bilayer membrane and that the compressibility of vesicles changes at a temperature $T_\Phi$ characteristic to the composition of said vesicles in the presence of the acoustic field.

14. The method according to claim 13, the vesicles comprising at least one of mammalian cells, yeast cells, fungus cells, bacteria, lipids, liposomes, exosomes, artificial drugs, and gene delivery vehicles.

15. The method according to claim 13, the lipids being phosphatidylcholines selected from 1,2-dimyristoyl-sn-glycero-3-phosphocholine (DMPC), 1,2-dipalmitoyl-sn-glycero-3-phosphocholine (DPPC), and 2-palmitoyl-2-oleoyl-sn-glycero-3-phosphocholine (POPC).

16. The method according to claim 13, each vesicle further comprising at least one sterol in its membrane.

17. The method according to claim 13, vesicles of a specific composition being separated when the device is tuned to a temperature higher than the $T_\Phi$ of said vesicles but lower than the $T_\Phi$ of vesicles of different compositions in the population.

18. The method according to claim 17, the compressibility of vesicles increasing as the device is tuned to a temperature higher than the $T_\Phi$ of said vesicles, causing said vesicles to migrate to an anti-nodal position with respect to the applied acoustic signals.

\* \* \* \* \*